United States Patent
Flynn et al.

(10) Patent No.: US 9,057,043 B2
(45) Date of Patent: Jun. 16, 2015

(54) METHODS AND MATERIALS FOR CULTIVATION AND/OR PROPAGATION OF A PHOTOSYNTHETIC ORGANISM

(71) Applicant: ForeLight, LLC, Blue Island, IL (US)

(72) Inventors: Adam Flynn, Blue Island, IL (US); Jeff Kantarek, Blue Island, IL (US)

(73) Assignee: Forelight, Inc., Chicago, IL (US)

( * ) Notice: Subject to any disclaimer, the term of this patent is extended or adjusted under 35 U.S.C. 154(b) by 0 days.

(21) Appl. No.: 13/833,079

(22) Filed: Mar. 15, 2013

(65) Prior Publication Data

US 2014/0011245 A1 Jan. 9, 2014

Related U.S. Application Data

(60) Provisional application No. 61/612,001, filed on Mar. 16, 2012.

(51) Int. Cl.
*C12M 1/02* (2006.01)
*C12M 1/00* (2006.01)
(Continued)

(52) U.S. Cl.
CPC ............ *C12M 21/02* (2013.01); *C12M 31/10* (2013.01); *C12M 41/24* (2013.01); *F21Y 2101/02* (2013.01); *F21Y 2111/007* (2013.01); *F21Y 2113/005* (2013.01); *F21K 9/30* (2013.01); *F21K 9/56* (2013.01); *C12P 39/00* (2013.01); *C12N 1/12* (2013.01); *C12P 7/6427* (2013.01); *C12M 23/48* (2013.01); *C12M 31/08* (2013.01); *C12M 41/48* (2013.01)

(58) Field of Classification Search
CPC ...... C12M 21/02; C12M 31/10; C12M 41/24; F21K 9/30; F21Y 2111/007; F21S 48/326
USPC ............... 435/292.1; 47/1.4; 362/231, 249.02
See application file for complete search history.

(56) References Cited

U.S. PATENT DOCUMENTS

| 6,992,333 B2 * | 1/2006 | Nagai et al. ...................... 257/88 |
| 2001/0014019 A1 * | 8/2001 | Begemann ..................... 362/231 |

(Continued)

FOREIGN PATENT DOCUMENTS

| CN | 101101948 A | * | 1/2008 |
| GB | 2469085 A | * | 10/2010 |

(Continued)

OTHER PUBLICATIONS

Rueping, M. et al. 2013. Visible Light Photoredox-Catalyzed Multicomponent Reactions. Organic Letters 15/9:2092-2095.*

(Continued)

*Primary Examiner* — William H Beisner
(74) *Attorney, Agent, or Firm* — Perkins Coie LLP

(57) ABSTRACT

The present disclosure provides methods and materials for the cultivation and/or propagation of a photosynthetic organism. Such methods may comprise the use of a lamp assembly that comprises a plurality of circuit boards, each comprising at least three edges, arranged in a substantially spherical shape defining an interior lamp assembly volume, wherein the plurality of circuit boards comprise a first planar surface in contact with the interior lamp assembly volume and an opposing second planar surface comprising light emitting diodes (LEDs); and a barrier that surrounds the plurality of circuit boards forming the substantially spherical shape.

32 Claims, 18 Drawing Sheets

(51) Int. Cl.
- *F21K 99/00* (2010.01)
- *C12P 39/00* (2006.01)
- *C12N 1/12* (2006.01)
- *C12P 7/64* (2006.01)
- *C12M 3/00* (2006.01)
- *C12M 1/36* (2006.01)
- *F21Y 101/02* (2006.01)
- *F21Y 111/00* (2006.01)
- *F21Y 113/00* (2006.01)

(56) References Cited

U.S. PATENT DOCUMENTS

| | | |
|---|---|---|
| 2009/0148931 A1 | 6/2009 | Wilkerson et al. |
| 2010/0028977 A1 | 2/2010 | Ng et al. |
| 2010/0128475 A1 | 5/2010 | Kovalchick et al. |
| 2010/0279395 A1 | 11/2010 | Haley, III |
| 2012/0238002 A1* | 9/2012 | Rittman et al. ............ 435/257.1 |

FOREIGN PATENT DOCUMENTS

| | | |
|---|---|---|
| JP | 2006319103 A * | 11/2006 |
| WO | WO 2007130359 A2 * | 11/2007 |

OTHER PUBLICATIONS

English language machine translation of CN101101948 (Jan. 9, 2008), pp. 1-5.*
English language machine translation of JP2006-319103 (Nov. 24, 2006), pp. 1-7.*
International Search Report for International Application No. PCT/US13/31922; Date of Mailing: Jun. 7, 2013; 2 pgs.
International Preliminary Report on Patentability and Written Opinion of International Application No. PCT/US13/31922; Date of Mailing: Sep. 16, 2014; 8 pgs.

* cited by examiner

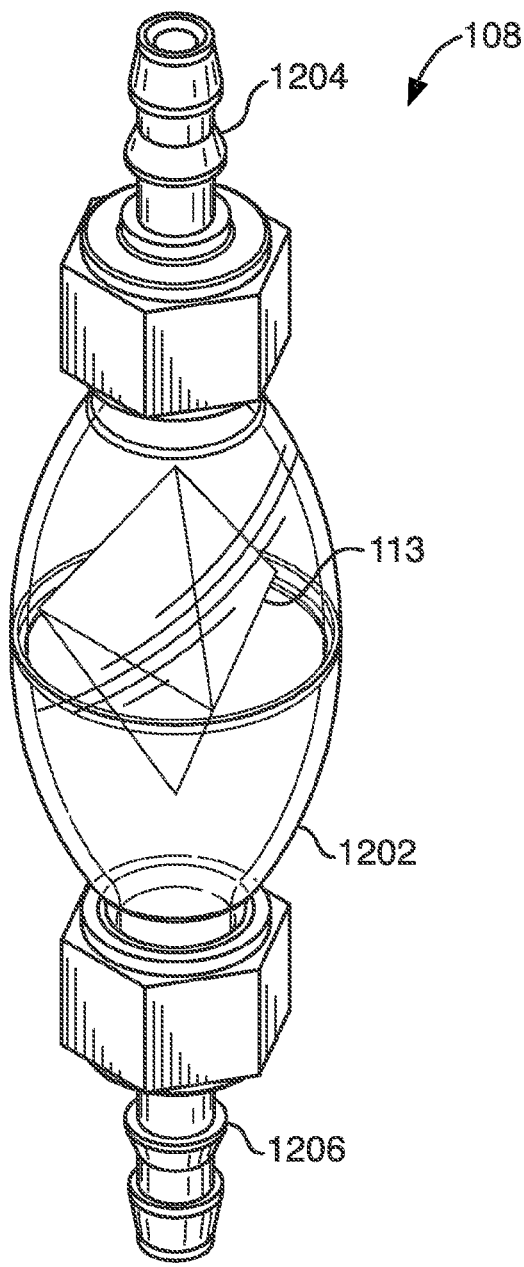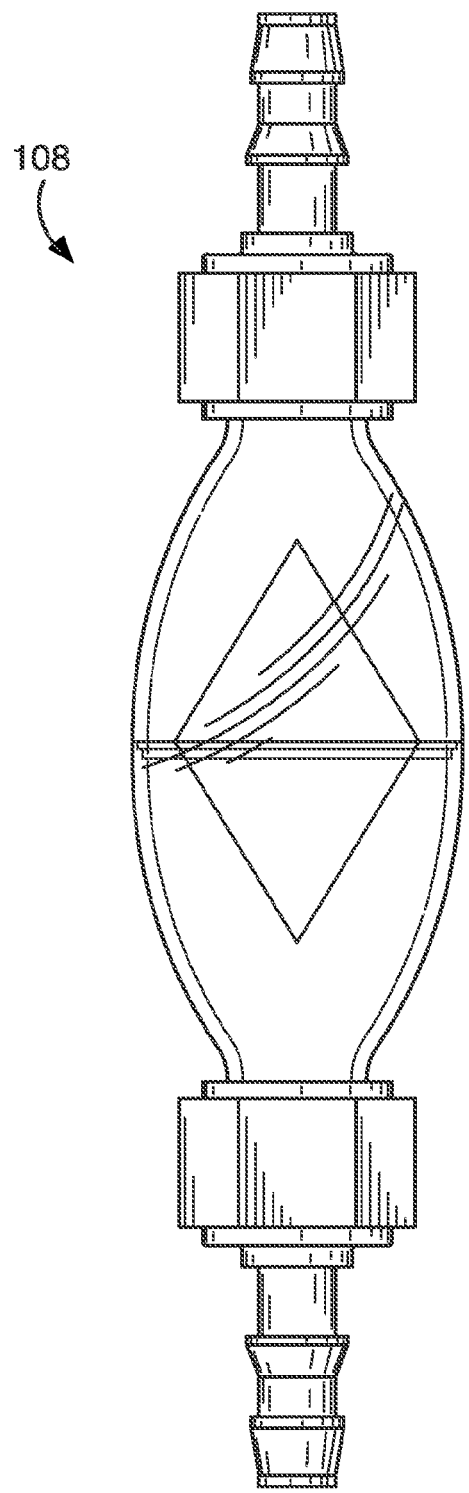
FIG. 12
FIG. 13

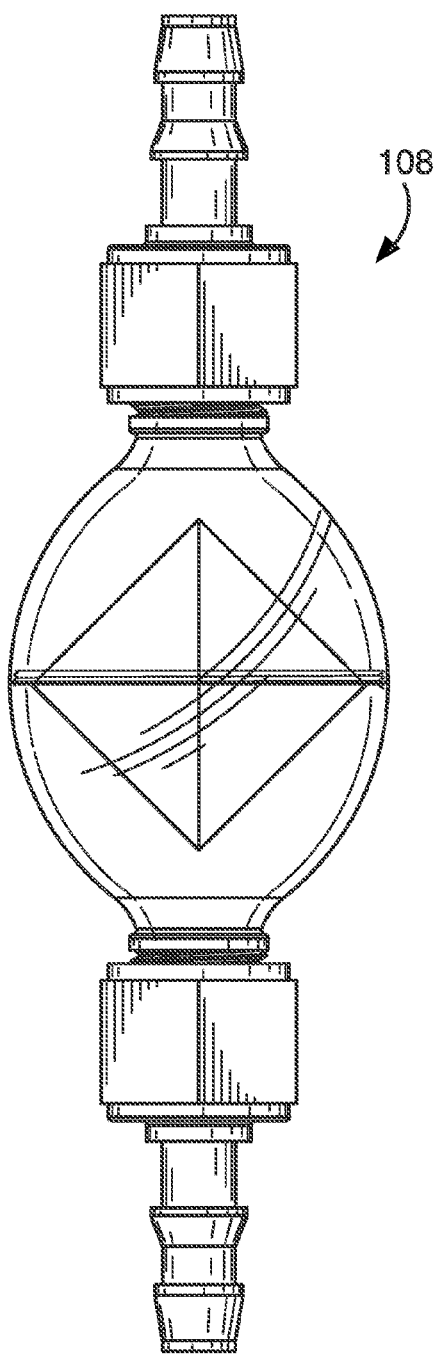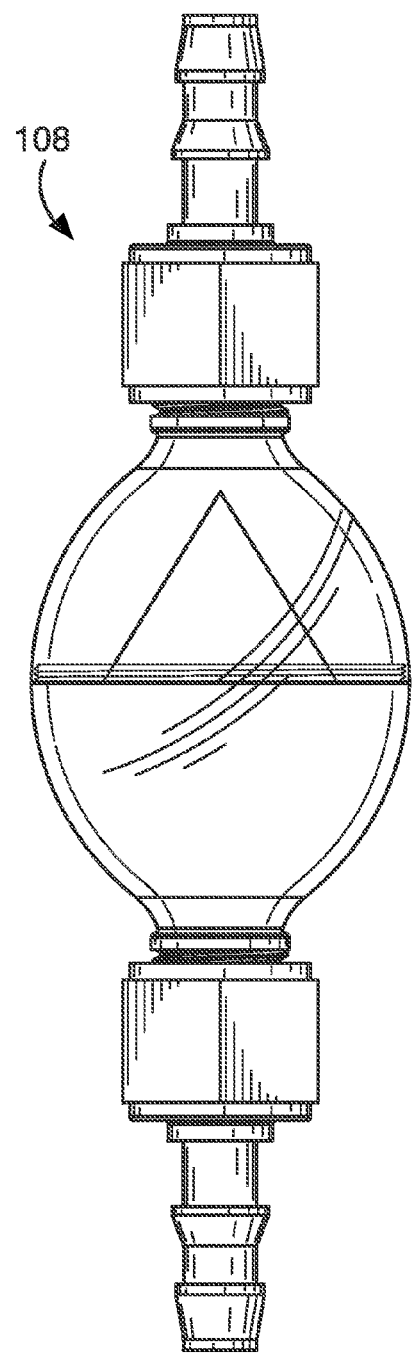
FIG. 25
FIG. 26

METHODS AND MATERIALS FOR CULTIVATION AND/OR PROPAGATION OF A PHOTOSYNTHETIC ORGANISM

CROSS REFERENCE TO RELATED APPLICATIONS

This application claims priority to U.S. Provisional Application Ser. No. 61/612,001 filed Mar. 16, 2012.

BACKGROUND

Photobioreactors have been described for the use of cultivating alga and generally employ shallow lagoons agitated with one or more paddle wheels. Such bioreactors are plagued with problems including poor production of algae due to seasonal and daily climatic changes and contamination. Given that such bioreactors are generally constructed to receive the sun's daylight light, productivity is limited by intensity of the sun which depends on the photoperiod and the season, among other factors.

SUMMARY

Methods and materials are provided for the cultivation including, for example, propagation of a photosynthetic organism.

The methods disclosed herein may comprise the use of a photobioreactor that comprises the use of an electromagnetic source in the visible light spectrum. In one embodiment, the electromagnetic source comprises a plurality of circuit boards. In another embodiment, each circuit board comprises at least three edges, arranged in a substantially spherical shape defining an interior lamp assembly volume. In another embodiment, the plurality of circuit boards arranged in a substantially spherical shape comprise a first planar surface in contact with the interior lamp assembly volume and an opposing second planar surface comprising high intensity lamps including, for example, light emitting diodes (LEDs). In another embodiment, the photobioreactor comprises a barrier that surrounds the plurality of circuit boards, said barrier having a substantially spherical, ovoid, egg, cylindrical, rectangular prismic or other similar shape. Such methods may be used to produce compounds (e.g., biomolecules) including, for example, fatty acids, phycobiliproteins such as C-Phycocyanin, allophycocyanin, phycoerythrin, biofuels such as phytol, and other various petrol fuel substitutes.

The present disclosure also provides a photobioreactor for cultivation and/or propagation of a photosynthetic organism. In one embodiment, the photobioreactor comprises an electromagnetic source in the visible light spectrum. In another embodiment, the photobioreactor comprises a vessel having a wall defining an interior vessel volume. In one embodiment, the vessel is substantially cylindrical, spherical, rectangular prismic or ovoid in shape. In another embodiment, the photobioreactor comprises a lamp assembly positioned within the interior vessel volume, wherein the lamp assembly optionally comprises a plurality of circuit boards, each optionally comprising at least three edges, arranged in a substantially spherical or ovoid shape defining an interior lamp assembly volume. In one embodiment, the plurality of circuit boards each comprise a first planar surface in contact with the interior lamp assembly volume and an opposing second planar surface comprising light emitting diodes (LEDs). In one embodiment, the photobioreactor comprises a barrier that surrounds the plurality of circuit boards. In one embodiment, the barrier is substantially cylindrical, spherical, rectangular prismic or ovoid in shape.

In some embodiments, which may be combined with any of the above or below embodiments, the barrier is cylindrical and comprises a cylindrical wall, an upper wall, and a lower wall each defining an interior tank volume.

In some embodiments, which may be combined with any of the above or below embodiments, the vessel is substantially spherical or ovoid.

In some embodiments, which may be combined with any of the above or below embodiments, the vessel comprises an opening for a gas inlet.

In some embodiments, which may be combined with any of the above or below embodiments, the vessel comprises an opening for a gas outlet.

In some embodiments, which may be combined with any of the above or below embodiments, the vessel comprises an opening for wiring the light source.

In some embodiments, which may be combined with any of the above or below embodiments, the lamp assembly is positioned substantially in the center of the vessel.

In some embodiments, which may be combined with any of the above or below embodiments, two or more lamp assemblies are positioned in the vessel.

In some embodiments, which may be combined with any of the above or below embodiments, the two or more lamp assemblies are positioned at different heights in the vessel.

In some embodiments, which may be combined with any of the above or below embodiments, three or more lamp assemblies are positioned in the vessel.

In some embodiments, which may be combined with any of the above or below embodiments, the three or more lamp assemblies are positioned at different heights in the vessel.

In some embodiments, which may be combined with any of the above or below embodiments, the three or more lamp assemblies are positioned in a helical arrangement in the vessel.

The present disclosure also provides a light source for use in cultivation and/or propagation of a photosynthetic organism. In one embodiment, the light source comprises: a plurality of circuit boards, each comprising at least three edges. In one embodiment, the circuit boards are arranged in a substantially spherical shape defining an interior lamp assembly volume, wherein the plurality of circuit boards comprise a first planar surface in contact with the interior lamp assembly volume and an opposing second planar surface comprising light emitting diodes (LEDs); and a barrier that surrounds the plurality of circuit boards forming the substantially spherical shape.

In some embodiments, which may be combined with any of the above or below embodiments, the substantially spherical shaped arrangement of the planar circuit boards has a side devoid of at least one circuit board to permit electrical connectivity. Alternatively the spherical shaped arrangement of the planer circuit boards has an aperture to permit electrical connectivity.

In some embodiments, which may be combined with any of the above or below embodiments, the circuit boards comprise two or more tabs around their perimeter that form one or more notches that permit the circuit boards to interlock.

In some embodiments, which may be combined with any of the above or below embodiments, the circuit boards are pentagon shaped.

In some embodiments, which may be combined with any of the above or below embodiments, eleven pentagons are joined to form a dodecahedron devoid of one side. In another embodiment, twelve pentagons are joined together to form a dodecahedron with an aperture in one or more of the pentagons.

In some embodiments, which may be combined with any of the above or below embodiments, the circuit boards are triangular shaped.

In some embodiments, which may be combined with any of the above or below embodiments, twenty triangles are joined to form an icosahedron devoid of one side. In another embodiment, twenty one triangles are joined to form an icosahedron with an aperture in one or more triangles.

In some embodiments, which may be combined with any of the above or below embodiments, the circuit boards comprise red, white, and blue LEDs.

In some embodiments, which may be combined with any of the above or below embodiments, the red, white, and blue LEDs are positioned adjacent to an LED of opposing color. In some embodiments, which may be combined with any of the above or below embodiments, the LEDs are pulse width modulated.

In some embodiments, which may be combined with any of the above or below embodiments, the barrier is plastic.

In some embodiments, which may be combined with any of the above or below embodiments, the barrier is substantially spherical or ovoid.

In some embodiments, which may be combined with any of the above or below embodiments, the plastic permits transmission of light.

In some embodiments, which may be combined with any of the above or below embodiments, the barrier has an opening to permit electrical connectivity.

In some embodiments, which may be combined with any of the above or below embodiments, a void between the barrier and the circuit boards comprises a fluid for dispersal of heat.

In some embodiments, which may be combined with any of the above or below embodiments, the fluid is mineral oil.

The present disclosure also provides methods of producing docosahexaenoic acid (DHA) comprising: providing one or more photosynthetic organisms comprising enzymes for generating DHA; adding the photosynthetic organisms to a vessel of a bioreactor, for example as described herein, comprising a liquid growth media; contacting the one or more photosynthetic organisms with light emitted from a lamp assembly. In one embodiment, the lamp assembly comprises a plurality of circuit boards. In another embodiment, each of the circuit boards are arranged in a substantially spherical shape defining an interior lamp assembly volume, wherein the plurality of circuit boards comprise a first planar surface in contact with the interior lamp assembly volume and an opposing second planar surface comprising light emitting diodes (LEDs). In one embodiment, the lamp assembly comprises a barrier that surrounds the plurality of circuit boards forming the substantially spherical or ovoid shape. In other embodiments, the plurality of circuit boards are arranged in a shape of any 4-, 6- or 8-sided triangular, planar geometric shape such as a tetrahedron, two-stacked tetrahedrons, an octahedron, or a 20 sided planar geometric shape, such as an icosahedron.

In some embodiments, which may be combined with any of the above or below embodiments, the one or more photosynthetic organisms comprise algae and/or a productive algal culture.

In some embodiments, which may be combined with any of the above or below embodiments, two or more algae are provided that have natural environments that are similar in salinity and dissimilar in temperature.

In some embodiments, which may be combined with any of the above or below embodiments, the algae are selected from the group consisting of *Isochrysis aff. Galbana, pavlova lutheri, arthrospira platensis, chlorella pyrenoidosa, synechococcus elongates*, including naturally occurring or genetically modified/recombinant strains of the foregoing.

In some embodiments, which may be combined with any of the above or below embodiments, the methods further comprise isolating the DHA from the growth media.

The present disclosure also provides methods for storage of a light energy comprising: providing one or more photosynthetic organisms comprising enzymes for generating one or more compounds from a light energy; adding the one or more photosynthetic organisms to a tank of a bioreactor comprising a liquid growth media; contacting the one or more photosynthetic organisms with light emitted from a lamp assembly, for example as set forth herein, and producing one or more compounds from the light energy. In one embodiment, the lamp assembly comprises: a plurality of circuit boards, each comprising at least three edges, arranged in a substantially spherical shape defining an interior lamp assembly volume, wherein the plurality of circuit boards comprise a first planar surface in contact with the interior lamp assembly volume and an opposing second planar surface comprising light emitting diodes (LEDs); and a barrier that surrounds the plurality of circuit boards forming the substantially spherical shape.

In some embodiments, which may be combined with any of the above or below embodiments, energy is subsequently released from the one or more compounds.

BRIEF DESCRIPTION OF THE DRAWINGS

The foregoing summary, as well as the following detailed description of the disclosure, will be better understood when read in conjunction with the appended figures. It should be understood that the disclosure is not limited to the precise arrangements, examples and instrumentalities shown.

FIGS. 12 to 28 are diagrams showing embodiments of lamp assemblies described herein.

DETAILED DESCRIPTION

The present disclosure provides methods and materials for the cultivation and/or propagation of a photosynthetic organism such as an alga using a photobioreactor. The photobioreactor provided herein comprises a lamp assembly that comprises a substantially spherical light source positioned in a vessel of the photobioreactor that comprises a liquid medium and a photosynthetic organism. The use of such a photobioreactor permits unexpectedly high growth and density of the photosynthetic organism thus maximizing bioconversion efficiencies and product yields from the photosynthetic organism. The methods provided herein may be used to produce one or more compounds (e.g., biomolecules) including but not limited to fatty acids such as docosahexaenoic add (DHA), docosapentaenoic acid (DPA), eicosapentaenoic acid (EPA) or other fatty acids or other compounds such as phycobiliproteins (e.g. C-Phycocyanin, Allophycocyanin, Phycoerythrin, etc), and biofuels such as phytol and other various petrol fuel substitutes) from the photosynthetic organism. Additionally or alternatively, such methods disclosed herein may be used to provide for storage of a light energy.

Figure 1:
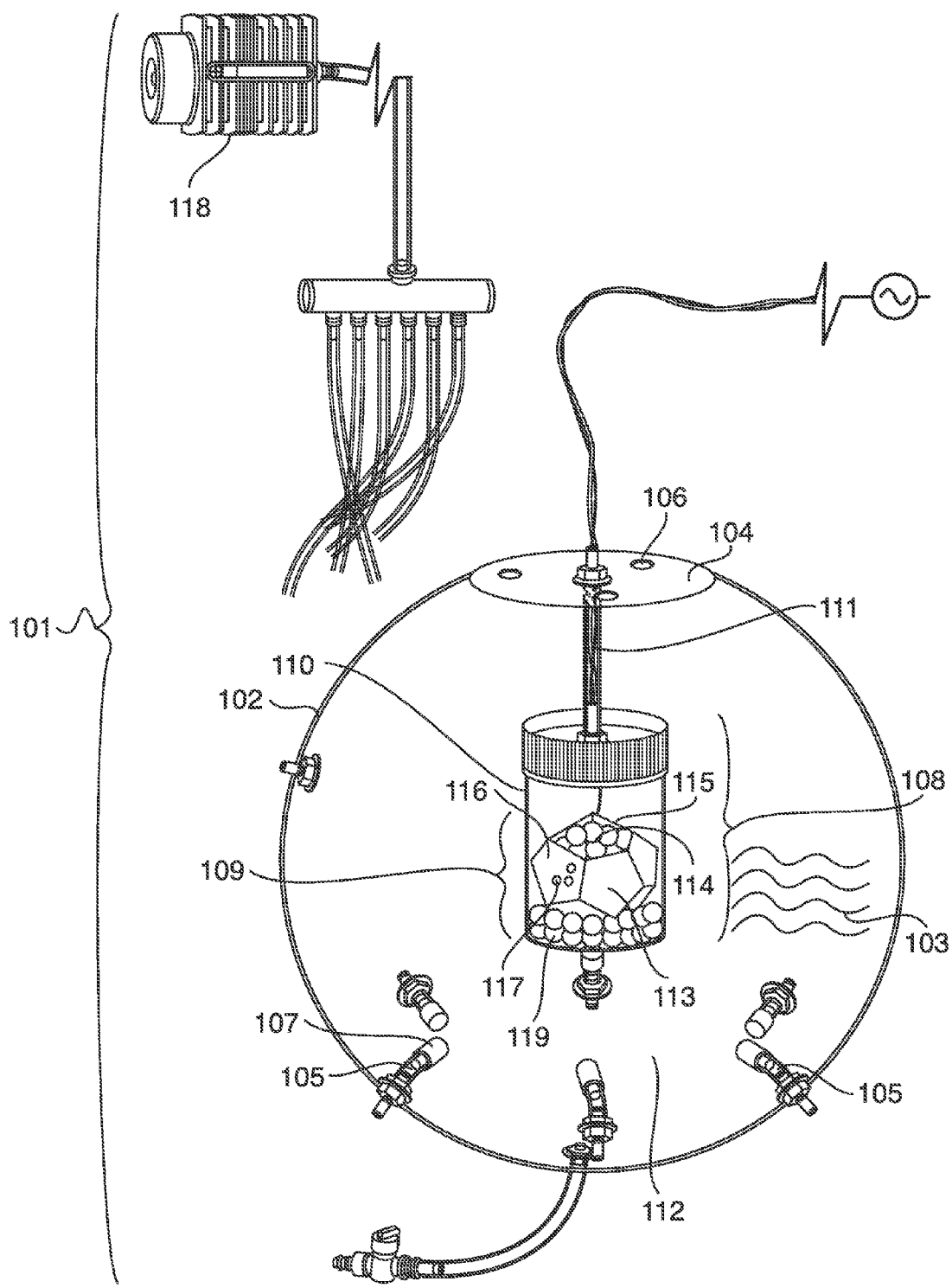
FIG. 1 shows a schematic of an exemplary spherical-shaped photobioreactor as described herein.

Referring now to FIG. 1, a photobioreactor in accordance with an embodiment of the present invention is shown. Photobioreactor 101 comprises a vessel 102 (e.g., a tank) for containing a liquid culture medium 103 for cultivating and/or propagating a photosynthetic organism.

The photobioreactor 101 of the invention is suitable for the culture of any kind of photosynthetic microorganism, such as a plant cell and unicellular or multicellular microorganisms having a light requirement. As used herein, the term "photosynthetic microorganism" also includes organisms genetically modified by techniques well known to one skilled in the art.

The liquid culture medium is sometimes referred to herein as an "algal" culture, but it will be appreciated that the photobioreactor may be employed for the cultivation of any type of photosynthetic microorganism.

The vessel 102 may be covered by lid 104. In one embodiment, lid 104 is constructed of an inert material including, for example, plastics such as polyvinyl chloride, high-density polyethylene, low-density polyethylene and polypropylene. The top rim of the vessel 102 may be formed into a lip which permits lid 104 to be secured (e.g., bolted or clamped) to the top of vessel 102. In addition, the top rim of vessel may be fitted with a gasket material to provide a liquid and gas-tight seal with lid 104. In an embodiment, lid 104 may be lined with a reflective material. In an embodiment, a rigid framing (e.g., metal framing) may be added to solidify the vessel.

Vessel 102 may comprise a hole for a gas inlet 105. In an embodiment, a portion of the gas inlet inside the vessel is capped with an air stone or metal foam 107. Additionally, vessel 102 may comprise gas vents 106 to permit exit of gas from the vessel.

The vessel 102 may be of any convenient shape, for example substantially spherical or cylindrical. Vessel 102 may be made of food grade or highly inert materials that do not leech and are corrosion resistant including, for example, plastics such as high-density polyethylene, low-density polyethylene and polypropylene. Alternatively, vessel 102 may be constructed of stainless steel, glass and the like. It is preferred that the vessel be constructed of a heat resistant material and/or a material that can withstand light pressurization.

A lamp assembly 108 (e.g. pebble) comprising light source 109, barrier 110, and an electrical connector 111 is suspended in the interior vessel volume 112. In an embodiment, the portion of the electrical connector 111 that resides inside the vessel is waterproofed. In one embodiment, the light source comprises a plurality of circuit boards 113, each comprising at least three edges, at least 4 edges or at least 5 edges, arranged in a substantially spherical shape defining an interior light source volume 114, wherein the plurality of circuit boards comprise a first planar surface 115 in contact with the interior light source volume and an opposing second planar surface 116 comprising high intensity lamps such as light emitting diodes (LEDs) 117 with an emission spectrum suitable for the growth of a photosynthetic organism; and a barrier 110 that surrounds the plurality of circuit boards forming the substantially spherical shape. Alternatively, a single circuit board (e.g., a flexible board) may be molded into a substantially spherical shape and used in the light assembly.

The circuit boards 116 may comprise red, white, and blue LEDs. Such LEDs may be positioned in groups containing two or more LEDs of the same color positioned adjacent to two or more LEDs of another color. Alternatively, an LED including, for example, a red, white, or blue LED, may be positioned adjacent to an LED of opposing color. In some embodiments, the LEDs may be positioned in rows such that a single LED is adjacent to four or six LEDs. The LEDs may emit light of uniform intensity or of varying intensity.

The substantially spherical shaped arrangement of the planar circuit boards may have an opening or a side devoid of at least one circuit board to permit electrical connectivity.

Figure 2A:
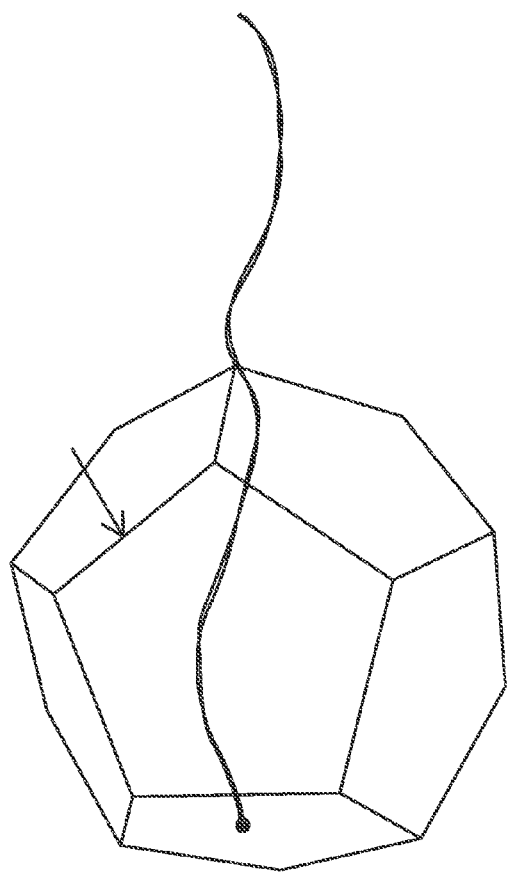
FIG. 2 shows a schematic of an exemplary dodecahedron shaped light source comprised of pentagonal-shaped circuit boards (A), an exemplary icosahedron shaped light source comprised of triangular-shaped circuit boards (B).
Figure 2B:
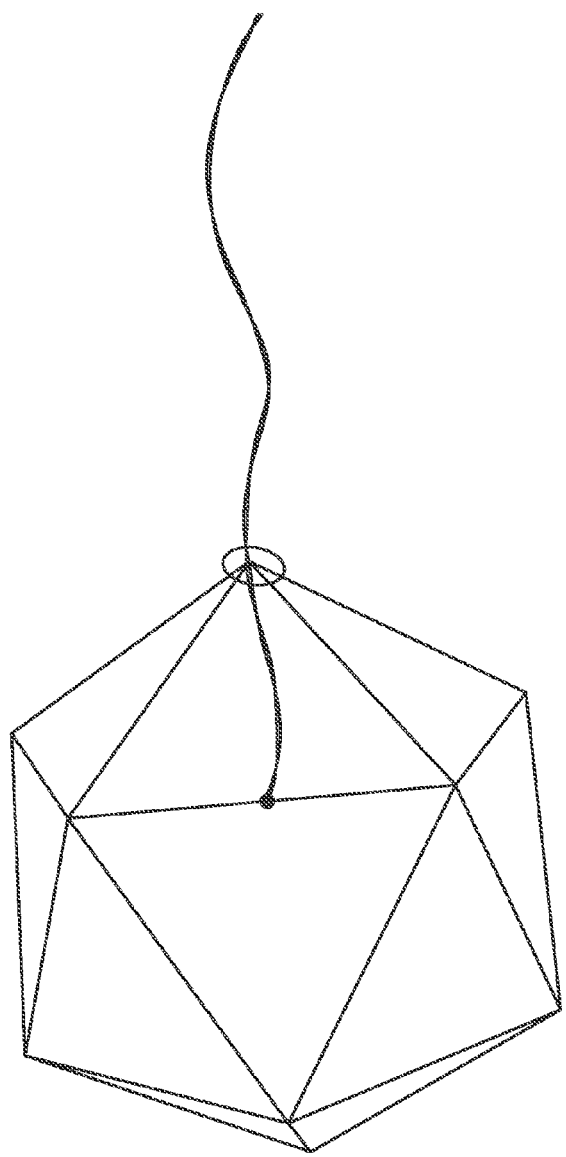

The circuit board may be of any polygonal shape. In one embodiment, the polygonal shape permits several circuit boards to be joined into a substantially spherical shape with an interior volume. In some embodiments, the circuit boards may be pentagon shaped. In a further embodiment, eleven pentagons are joined to form a dodecahedron devoid of one side (FIG. 2A). Alternatively, in some embodiments, the circuit boards may be triangular in shape. In a further embodiment, twenty triangles are joined to form an icosahedron devoid of one side (FIG. 2B). In another embodiment, six triangles are joined to form a double pyramid with a triangular base (FIG. 2C). In another embodiment, eight triangles are joined to form a double pyramid with a square base (FIG. 2D).

The circuit boards may also comprise a copper or other metal layer that faces the interior volume for dissipation of heat from the lamps (e.g., LEDs) or signaling.

Figure 3A:
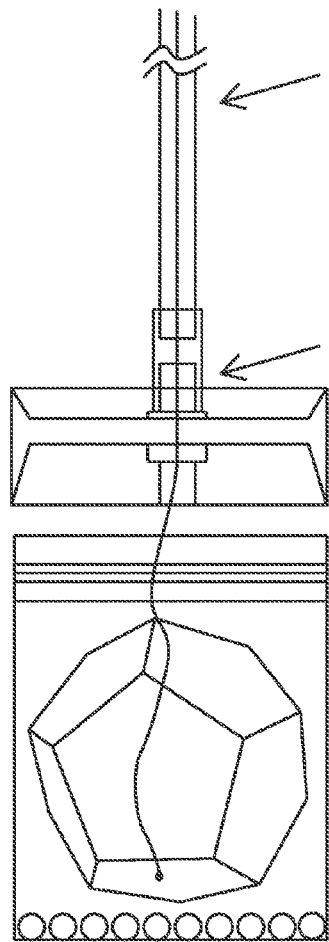
FIG. 3 shows a schematic of an exemplary lamp assembly comprising a light source comprised of pentagonal-shaped circuit boards (A), an exemplary lamp assembly comprising a light source comprised of triangular-shaped circuit boards (B).
Figure 3B:
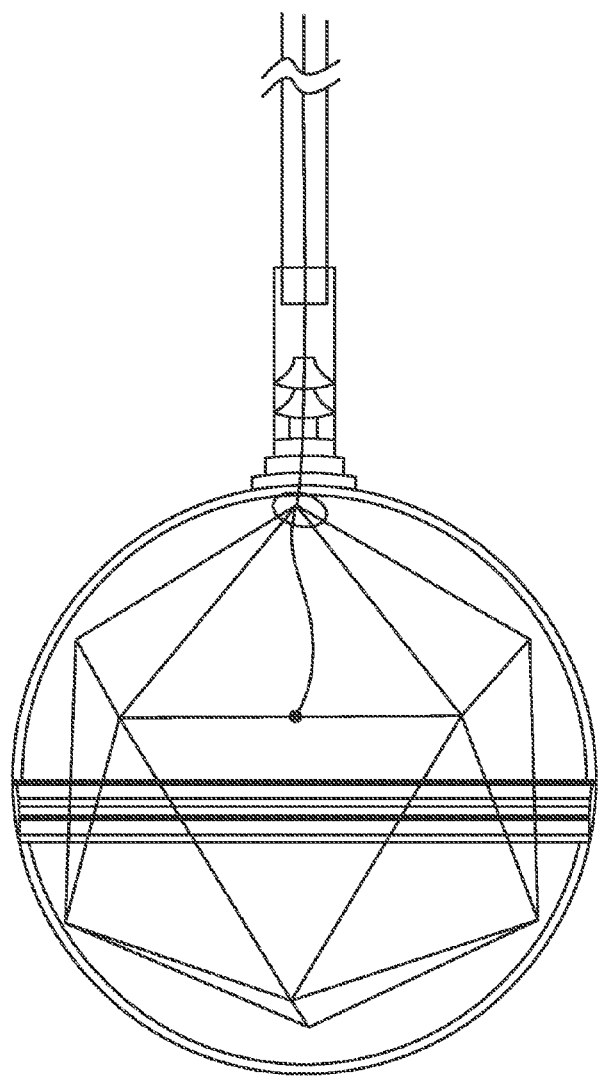

In some embodiments, the circuit boards comprise two or more tabs around their perimeter that form one or more notches that permit the circuit boards to interlock (see for example FIG. 3A (triangle) and FIG. 3B (pentagon).

The barrier 110 surrounding the plurality of circuit boards forming the substantially spherical shape may be constructed of a variety of inert materials, such as various plastic materials including, for example, transparent plastic and/or plastic tolerant to extreme temperatures. The barrier functions to provide a water-tight seal around the plurality of circuit boards to prevent a culture medium in the interior vessel volume 112 coming in contact with the plurality of circuit boards 116. In some embodiments, the barrier 110 surrounding the plurality of circuit boards forms a container (e.g., a jar) around the circuit boards which may be substantially cylindrical (FIG. 3A) or spherical (FIG. 3B) in shape. In some embodiments, the container formed by the barrier holds one or more objects to reduce the buoyancy of the light source (e.g., inert beads such as glass beads 119).

The circuit board may be populated with LEDs that emit light of one or more wavelengths to optimize for a particular strain of photosynthetic life or to express a specific feature for abnormal growth. In some embodiments, the circuit boards may be populated with lamps that emit electromagnetic radiation outside the visible spectrum including, for example, UV and/or IR light. Such lamps may be used to sterilize the liquid media in the vessel (e.g., lamps emitting UV light) and/or heat the liquid media in the vessel (e.g., lamps emitting IR light). In some embodiments, the LEDs may be pulse width modulated. In one embodiment, the pulse width modulation is optimized to maximize growth of the particular microorganism in the photobioreactor. In another embodiment, the duty cycle is at least 50%, at least 55%, at least 50%, at least 55%, at least 60%, at least 65%, at least 70%, at least 75%, at least 80%, at least 85%, at least 90%, or at least 95%.

The circuit board may comprise sensors for collecting data from the interior of the vessel. For example, sensors may be configured to collect data on the culture media including, for example, optical density, pH, and/or conductivity.

The plurality of circuit boards forming a substantially spherical shape with an interior volume may comprise one or more microprocessors in the interior volume including for individual control of LEDs or control of banks of LEDS (e.g., two or more LEDs) and/or feedback monitoring.

Vessel 102 may comprise one or more holes or access ports for providing electrical connectivity to the lamp assembly 108.

Figure 4:
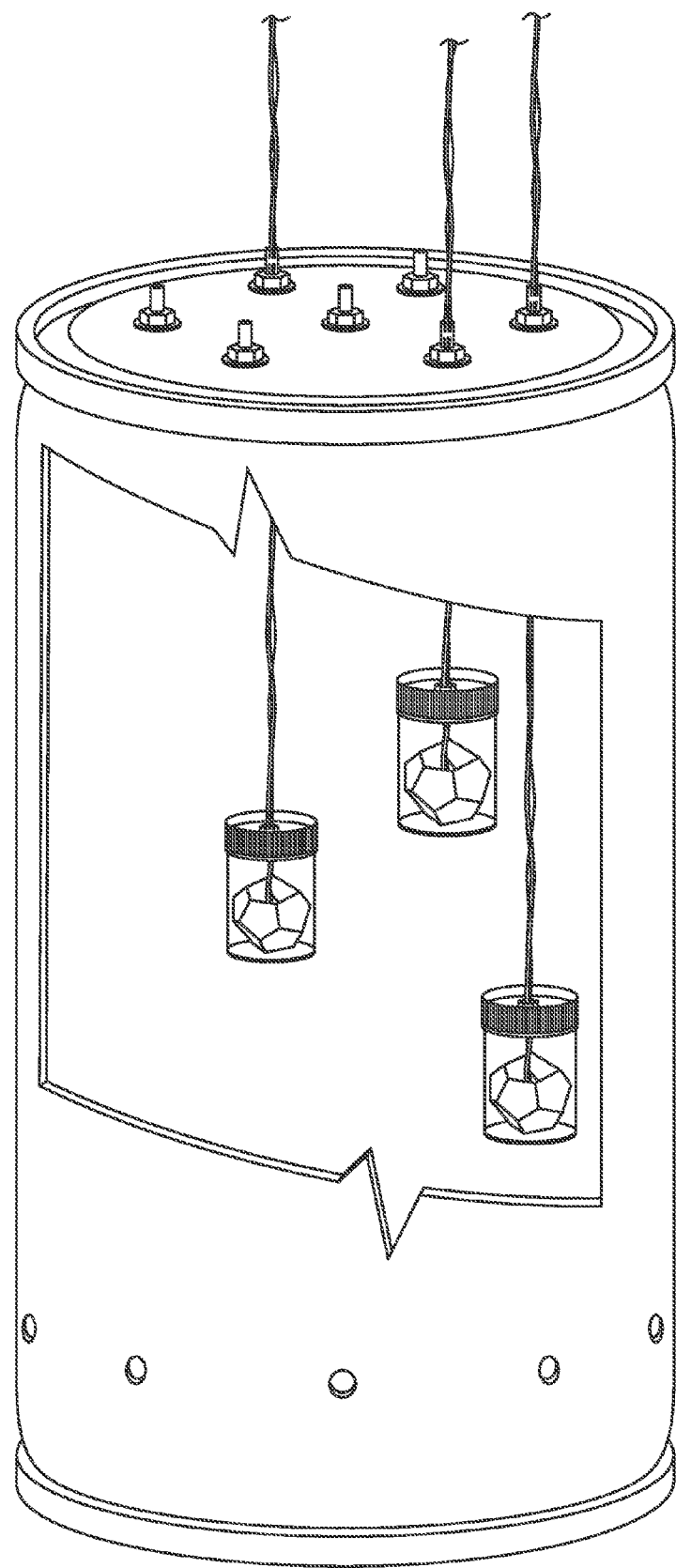
FIG. 4 shows a schematic of the interior of an exemplary vertical barrel-shaped photobioreactor as described herein.

One or more lamp assemblies 108 may be distributed throughout the interior vessel volume 112. A single light source may be suspended at the center of the interior vessel volume. Alternatively, when two or more lamp assemblies are used in the photobioreactor, the lamp assemblies may be suspended at the same or different heights in the interior vessel volume (see FIGS. 1 and 4). Alternatively, when three or more lamp assemblies are used, the lamp assemblies may be suspended in any geometric arrangement such as a helical or double helical arrangement.

A cooling device may be provided to control the temperature of the vessel. Such cooling device may be in the form of a cooling jacket surrounding a portion of the wall of vessel 102. Such cooling jacket provides circulating cooling water or other fluid across the wall of vessel 102 to absorb heat and assist in controlling the temperature of culture medium 103 contained in the vessel. Cooling water may enter jacket through an inlet tube and exit through an exit tube. The dimensions of the cooling jacket will depend upon a number of factors, such as the amount of heat transmitted by lamp assemblies 108 to the liquid culture medium contained in vessel 102, the desired temperature of the culture medium, the temperature and flow rate of the cooling water, and the like. Alternatively, temperature of the vessel may be regulated via temperature regulation of the lamp assemblies or LEDs, for example by circulating and/or controlling temperature of an oil in which the LEDs or lamp assembly is immersed.

Vessel 102 is generally designed to accommodate a head space between the liquid culture surface and lid. The head space allows for foaming, which often occurs in biological culture media.

Vessel 102 may be fitted with gas inlet tube 105 which is provided with a pressurized gas (e.g., carbon dioxide or carbon dioxide-enriched air) for supporting the photosynthetic requirements of the algal culture. Tube 105 passes through the wall of vessel 102. Gas bubbles rise through the liquid algal culture medium contained in vessel 102 and the spent gases escape through gas vents 106 which may be disposed in the wall or lid of vessel, preferably above the surface level of the culture medium.

If more vigorous mixing is desired, an air pump 118 or other agitation mechanism, for example powered by a motor, may be used to agitate the culture medium.

The photobioreactor 101 may further comprise a cleaning unit mounted within the interior vessel volume or on the outside surface of the lamp assembly 108 for cleaning the outer surface of the lamp assembly, and a cleaning unit actuator for actuating the cleaning unit. Such a cleaning unit may function to get rid of the cultivated and/or propagated photosynthetic organisms which may block the light source by adhering to the outer lamp assembly. In some embodiments, the vessel is composed of or coated with a superhydrophobic, hydrophilic, and/and or oleophobic material.

Figure 5:
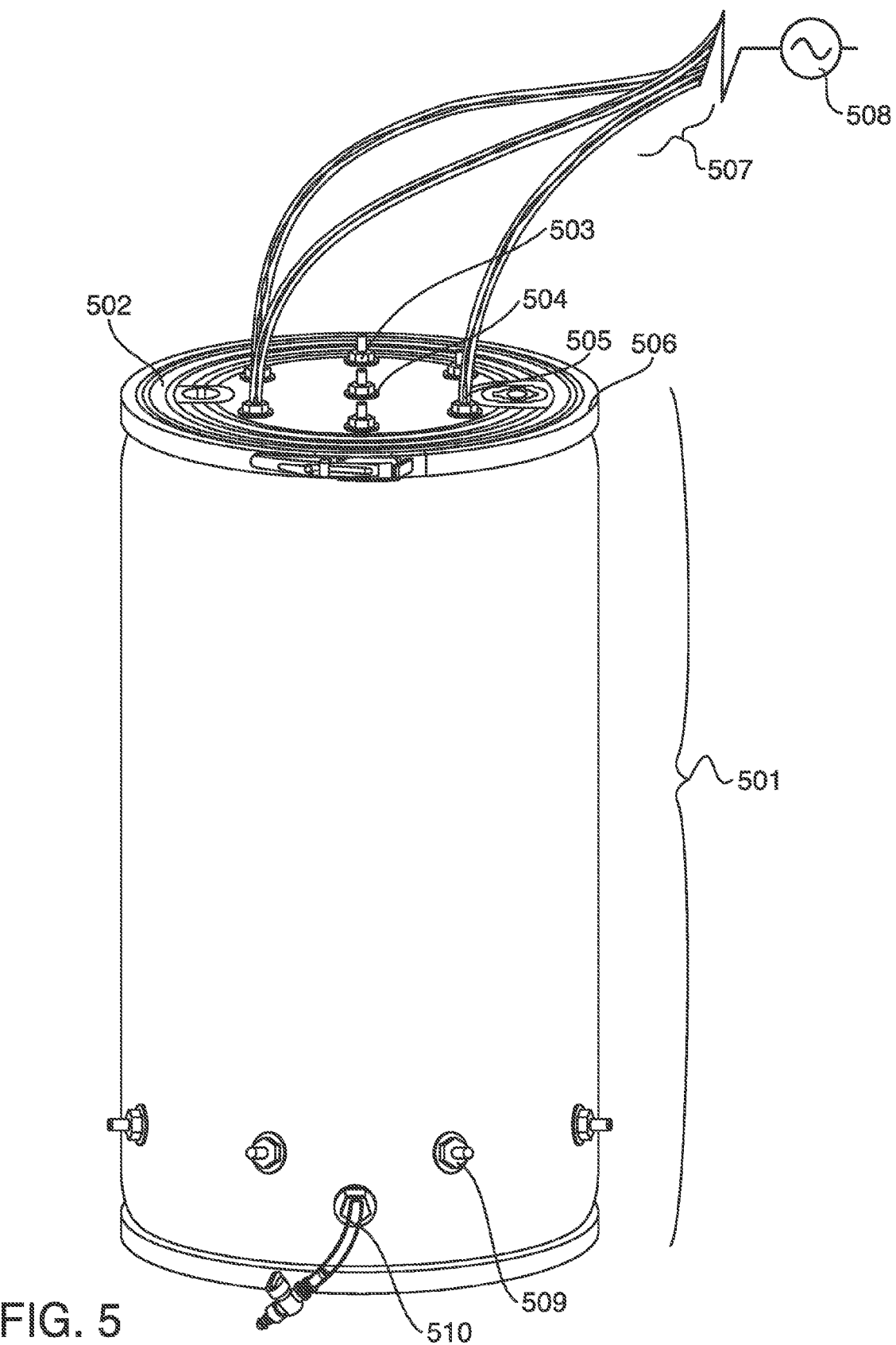
FIG. 5 shows a schematic of an exemplary vertical barrel-shaped photobioreactor as described herein.

Referring now to FIG. 5, this figure shows another embodiment of a photobioreactor as provided by the instant disclosure. Such a photobioreactor may comprise a cylindrical shaped vessel 501 (e.g., a barrel shaped vessel) to permit stacking or racking of the two or more vessels in a vertical or horizontal position. Because of their general availability, cost, and ease of storage (e.g., stackability), 55 gallon plastic drums can be employed with the methods disclosed herein. In an embodiment, the vessel 501 may be lined with a reflective material. In an embodiment, the vessel comprises a lid 502 with gas exhaust fittings 503, a $CO_2$ injection line 504, and electrical inlet fittings 505. In an embodiment, the lid may be attached to the vessel via an attachment mechanism such as a clamp 506. The electrical inlet fittings 505 may receive waterproofed electrical lines 507 powered by power source 508. In some embodiments, the vessel may comprise air line bulkhead fittings 509 and water line bulkhead fittings 510.

Although the embodiment shown in FIG. 5 is depicted in a vertical configuration, a photobioreactor consistent with the instant disclosure may also be arranged in a horizontal configuration. Such a photobioreactor may comprise a cylindrical shaped vessel (e.g., a barrel shaped vessel) to permit stacking or racking of the two or more vessels in a horizontal position. In one embodiment, the vessel comprises a lid for introducing medium or removing culture and a drain for introducing medium or removing culture. In another embodiment, the photobioreactor comprises a gas inlet positioned on the bottom of the photobioreactor. In one embodiment, this gas inlet is a $CO_2$ inlet. In another embodiment, the photobioreactor comprises one to a plurality (e.g. 1 to about 50, 2 to about 30, 3 to about 20 or about 6, 8, 10 or 12) bottom gas fittings and one to a plurality (e.g. 1 to about 50, 2 to about 30, 3 to about 20 or about 6, 8, 10 or 12) of top gas fittings. In one embodiment, as viewed from the base end of the vessel with the drain at the bottom, the bottom gas fittings are located substantially between about the 3- and about the 6-o'clock positions, for example about the 3-, about the 3:30-, about the 4-, about the 4:30-, about the 5-, about the 5:30- or about the 6-o'clock positions. In one embodiment, as viewed from the base end of the vessel with the drain at the bottom, the top gas fittings are located substantially between about the 9- and the 12-o'clock positions, for example about the 9-, about the 9:30-, about the 10-, about the 10:30-, about the 11-, about the 11:30- or about the 12-o'clock positions. In one embodiment, air is circulated in and out of the vessel via the bottom gas fittings and the top gas fittings. In one embodiment, gas enters the vessel via the bottom gas fittings and exits the vessel via to gas fittings. In one embodiment, the vessel contains volume markers, for example gallon markers.

The photobioreactor may further comprise a transferring mechanism for transferring liquid media, nutrients and/or antibacterial agents to the interior vessel volume. Nutrients may include synthetic and/or organic nutrients. In some embodiments, an anti-bacterial agent (e.g., a detergent) may be added to the liquid media to slow, or prevent, the growth of contagens (e.g., any organism that is other than the photosynthetic microorganism purposefully added to the vessel) in the vessel. Nutrients and/or antibacterial agents may be added to the vessel by any method known in the art including, for example, via an automated drip system. In an embodiment, the automated drip system may be connected (e.g., wired or wireless connection) to a monitoring system that monitors nutrient levels in the vessel. Such a monitoring system may constantly or periodically monitor nutrient levels in the vessel and prompt the automated drip system to release nutrients into the vessel when nutrient levels fall below a predetermined limit. Conversely, the monitoring system may prompt the automated drip system to stop the release of nutrients into the vessel when nutrient levels exceed a predetermined limit. In some embodiments, other trace chemicals (e.g., citric acid) may be added to the vessel to optimize environmental conditions for the growth of the photosynthetic microorganism.

FIGS. 6A to 6F show embodiments of lamp assemblies 108 included within a vessel 102. In each of these embodiments, the lamp assemblies 108 are configured to be interconnected in series along one or more connection lines 602. This connection scheme enables power to be provided to more than one lamp assembly 108 within a vessel. The configurations of the light assemblies 108 within the vessels 102 are based on the strain in question and the targeted product. For example, certain strains may have better growth rates when only one connection line 602 is disposed within a vessel while other strains have better growth rates when more than one connection line is disposed within a vessel.

While FIGS. 6A to 6F show the connections being made in series, the lamp assemblies 108 may include parallel electrical connections so that a failure of one lamp assembly does not affect the operation of other interconnected lamp assemblies. Further, while the connection lines 602 are shown as being substantially straight through the vessels 102, in other embodiments, the connection lines 602 may be formed at one or more angles (e.g., lamp assemblies 108 may be connected at a 90 degree angle).

The example connection line 602 is configured to provide at least one of power and immersion oil to each of the lamp assemblies 108. For example, in FIG. 6A the vessel 102a includes connection line 602a, which includes ports 604a and 604b. The immersion oil is provided to the connection line 602a through port 604a and exits the connection line 602a at port 604b. In this manner, an operator can cycle immersion oil through the lamp assemblies 108 connected to the connection line 602a to control temperature. In addition, electrical connector 111 is provided to each of the lamp assemblies 108 through port 604a. The control of power and oil to the lamp assemblies 108 is described in further detail in conjunction with FIGS. 9 and 10.

Figure 6A:
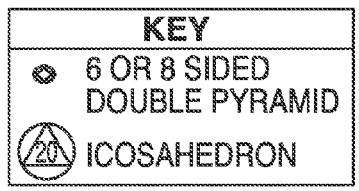
FIGS. 6A-F show various positions of lamp assemblies within a horizontal barrel shaped photobioreactor as described herein.
Figure 6A:
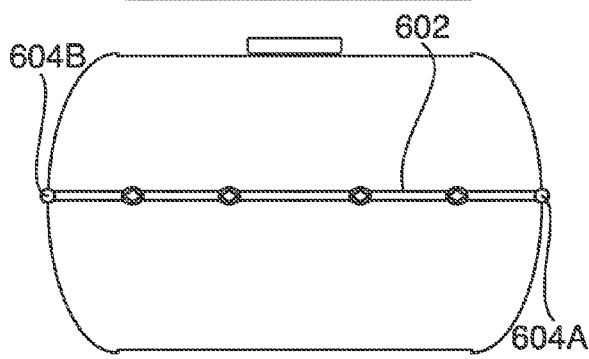
Figure 6B:
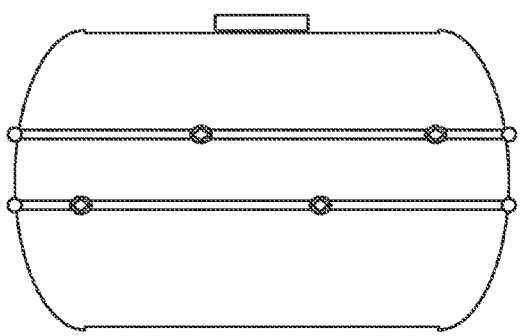
Figure 6C:
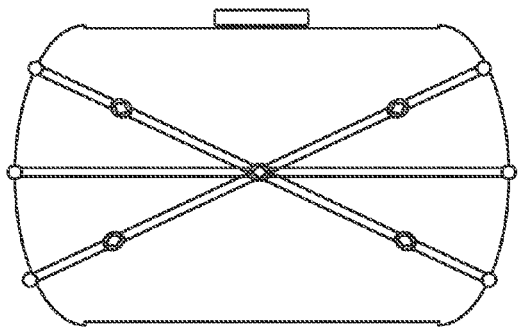

FIG. 6C shows that connection lines 602 may interconnect. This interconnection facilitates the flow of immersion oil through the vessel 102. Additionally or alternatively, the interconnection may enable lamp assemblies 108 located at intersection points to be controlled by either of the control signals on the intersecting electrical connectors 111. For instance, the lamp assembly 108c may be connected to electrical connectors 111 positioned within respective ports 604c, 604d, and 604e. As a result, the lamp assembly 108c may be controlled by a control signal provided on any one of the electrical connectors 111.

Figure 6D:
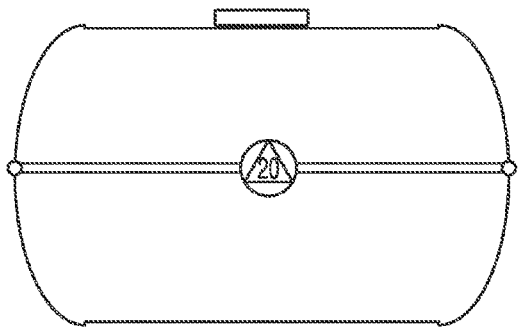
Figure 6E:
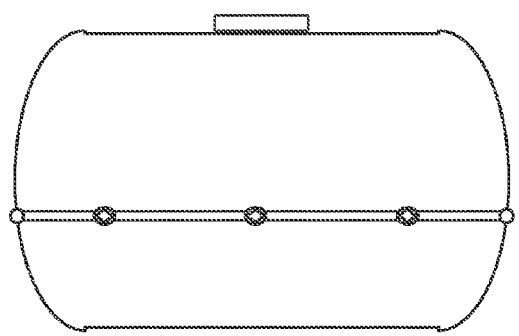
Figure 6F:
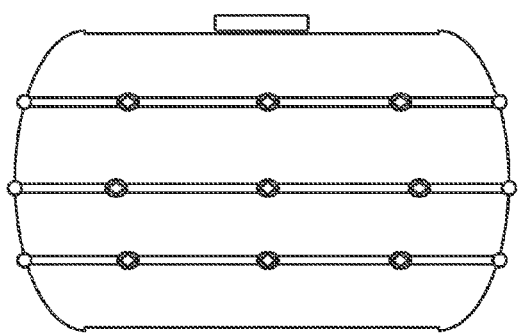

FIG. 6D shows a connection line 602 with a lamp assembly 108 that includes twenty circuit boards with LEDs. In this embodiment, immersion oil is cycled though the lamp assembly 108 to control temperature. Further, the configuration of the twenty circuit boards enables light to be directed to substantially any location within the vessel 102. This is in comparison to the light assemblies 108 of FIGS. 6A, 6B, 6C, 6E, and 6F that include relatively fewer circuit boards. These figures accordingly use more light assemblies to compensate for each light assembly having fewer LEDs.

A large scale photobioreactor is also contemplated by the present disclosure. Such a bioreactor may comprise one or more vessels and one, two or more lamp assemblies. The vessels may be of uniform volume and dimension or may be of varying volume and dimension. For example, vessels that hold 55 gallons or greater, or vessels that hold 3,000 gallons or greater, may be used in the large scale photobioreactors disclosed herein. In an embodiment, area may be provided between vessels to provide for connectivity of one vessel to another. In another embodiment, the vessel may have a central column for light distribution and/or electrical connectivity.

Figure 7:
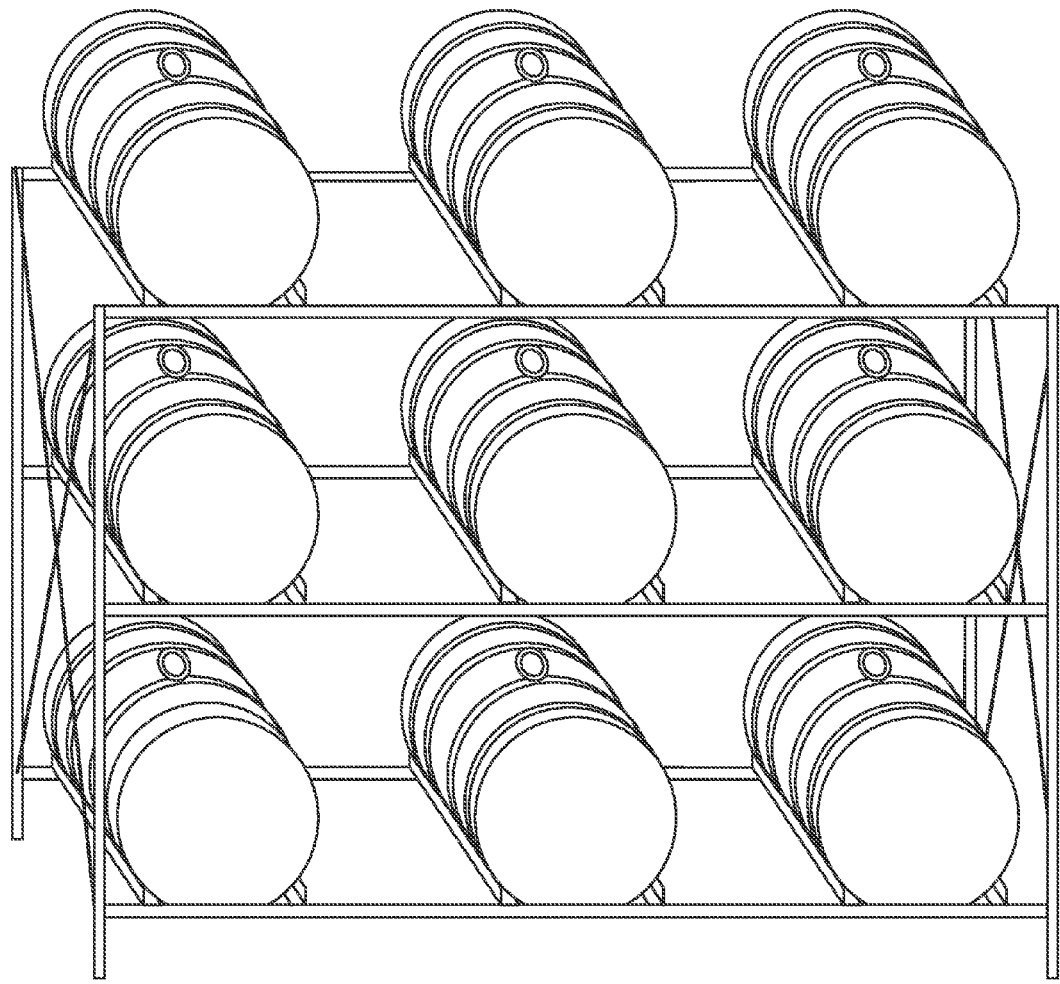
FIG. 7 shows an exemplary rack configuration for horizontal barrel shaped photobioreactors as described herein.
Figure 8B:
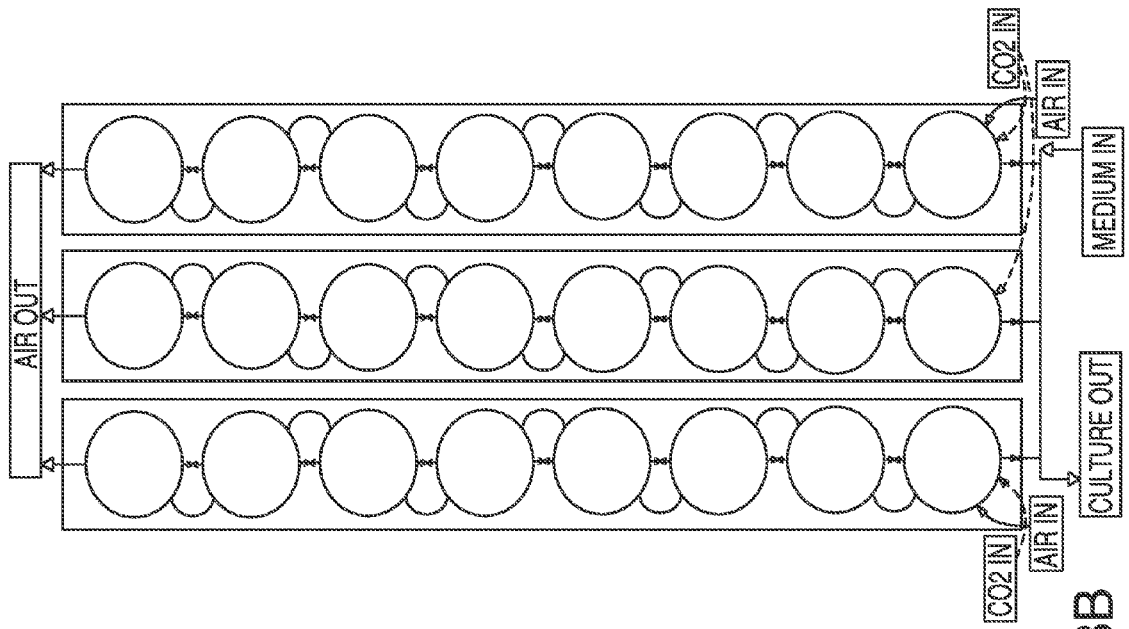
FIG. 8 shows an exemplary rack connection configuration for horizontal barrel shaped photobioreactors A and B as described herein.
Figure 8A:
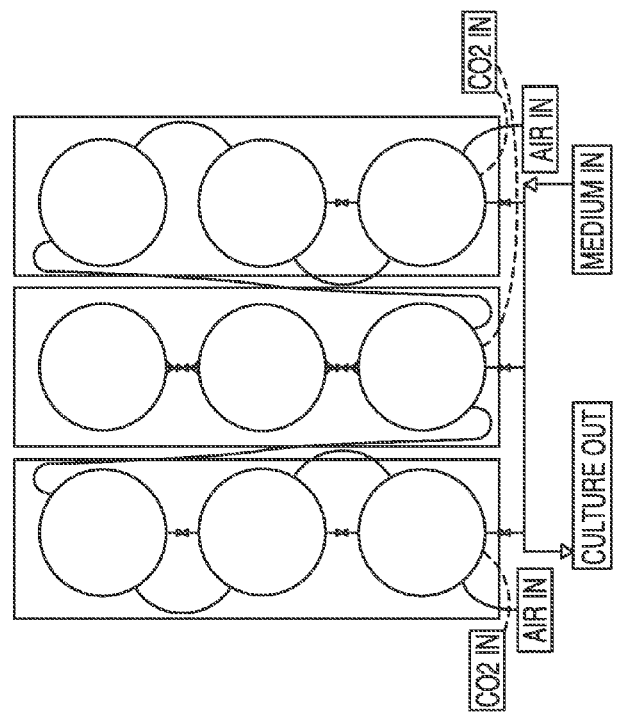

It will be appreciated that the photobioreactors of the invention can be produced in widely varying sizes. Several photobioreactors may be grouped together to produce large scale photobioreactors for example as shown in FIGS. 7 and 8. For simplicity, a single photobioreactor employing one light assembly has been illustrated in FIG. 1, however, in a typical industrial scale photobioreactor, 2, 3, 4, 5, 6, 7, 8, 9, 10, 20, 30, 40, 50, 60, 70, 80, 90, 100 or more photobioreactors each comprising one or more lamp assemblies may be used.

A photobioreactor with two or more vessels may comprise air and water lines that connect a vessel with one or more adjacent vessels. The air and water lines may comprise valves to direct the flow of air and/or water in a predetermined manner. Optionally, the valves may permit for quick disconnection of a vessel for maintenance and/or inspection. FIGS. 7 and 8 show diagrams of photobioreactor embodiments including multiple interconnected vessels. In particular, FIG. 7 shows a photobioreactor embodiment with multiple columns of vessels wherein each column of vessels is interconnected to another column of vessels. FIG. 8 shows a photobioreactor embodiment wherein multiple vessels in a single column are interconnected.

In the illustrated embodiment of FIGS. 7 and 8, air enters in through the twelve gas inlets at the 7:30 and 4:30 positions on the barrel where the stream is broken up into a column of two micron bubbles, which mix with the culture medium, adding circulation and necessary gases. For strains with lower gas requirements it is possible to subdivide the gas inlets using a fraction of the inlets for gas and leaving the remainder of the inlets unused or connected to a water recirculation pump. In this embodiment, a gas bubble builds at the top of the lower barrels until the gas reaches the 11:30 and 12:30 positions of the gas outlet. At this point, the pressure of the bubble drives the same process in the barrel above until the gas reaches the top of the column. It should also be noted that the bottom barrel of each column includes between two and four additional gas inlets coupled to 0.5 micron diffusers, which allow for the utilization of more exotic gases for gross supplementation (i.e. $CO_2$, gaseous ammonia, etc.).

In some embodiments, a large scale photobioreactor may comprise a single injection point for air and/or nutrients such that the introduction of air (e.g., $CO_2$) and/or nutrients into a first vessel operably connected with other vessels allows the air and/or nutrients to move from the first vessel into the other vessels.

The vessels of a large scale photobioreactor may be operably connected to a control unit (e.g., a controller or a server) and/or sensor monitoring unit. In some embodiments, the control unit may be configured to permit an operator to control the lamp assembly in each vessel (e.g., turn the lamp assembly on or off, or adjust the intensity of the lamps). In some embodiments, the sensor unit may be configured to disconnect a vessel from other vessels in the photobioreactor upon sensing that the vessel has been contaminated.

Figure 9:
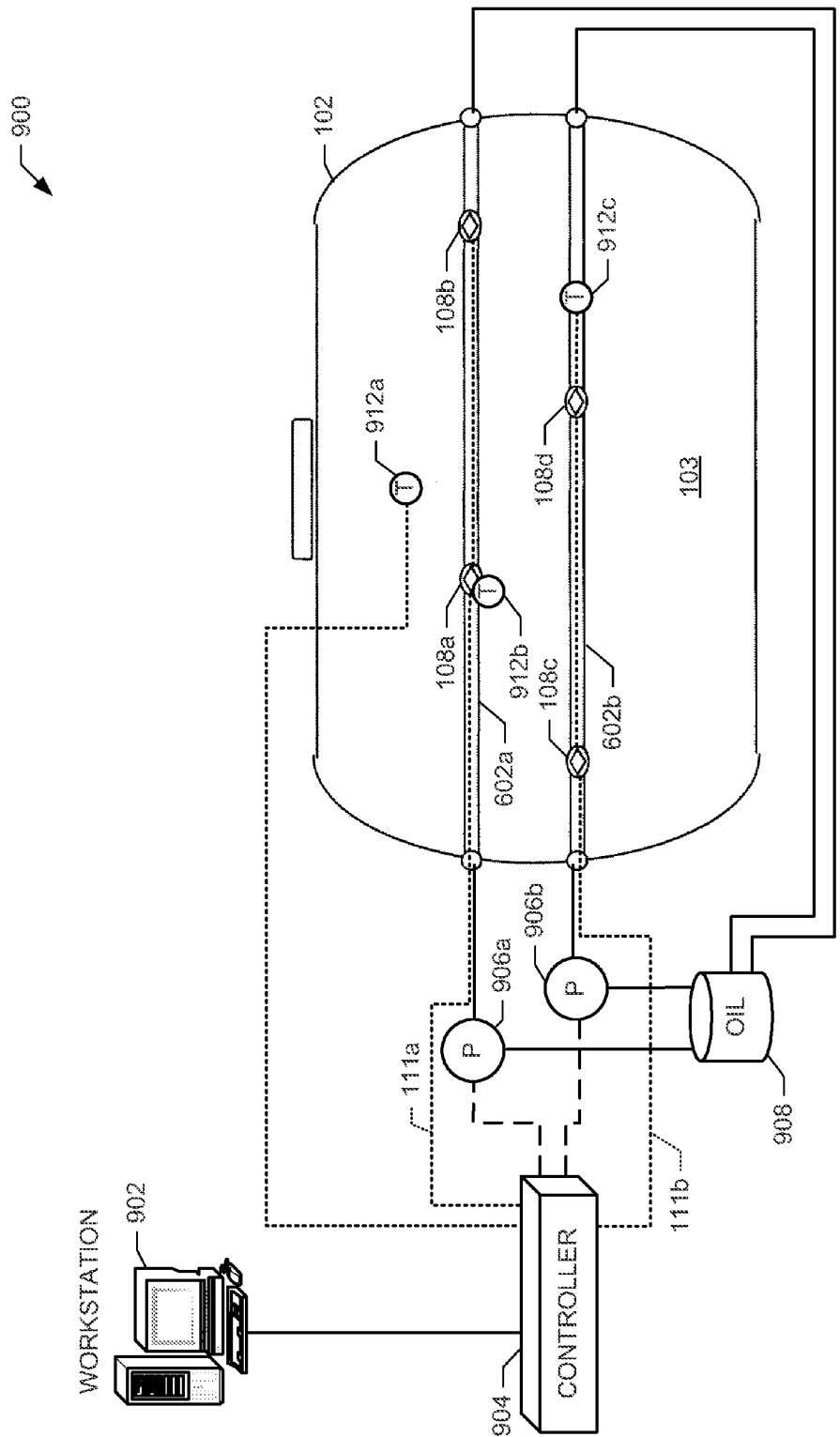
FIG. 9 shows a block diagram of an example control system for managing the growth of cultures, according to an example embodiment of the present invention.

A high level block diagram of an example control system 900 is illustrated in FIG. 9. The example control system 900 includes a workstation 902, a controller 904 (e.g., a control unit), a vessel 102, pumps 906, and an immersion oil container 908. While FIG. 9 shows the controller 904 providing control for only the vessel 102, in other embodiments the controller 904 may be communicatively coupled to two or more vessels. Further, the workstation 902 may be communicatively coupled to more than one controller.

The example workstation 902 is configured to provide an operator interface for providing instructions to the controller 904, controlling of the process, and displaying system process data. The example controller 904 manages the control of lamp assemblies 108 and the flow of immersion oil. In other examples, the controller 904 can be configured to manage the control of the liquid culture medium 103 within the vessel 102. For instance, the controller 904 may be configured to control gas inlet valves, gas vents, fluid inlet valves, and/or additive valves.

The example workstation 902 operates in conjunction with the controller 904 to provide control and system feedback to an operator. The workstation 902 includes any type of processor including, for example, a personal computer, a laptop, a server, a smartphone, a tablet computer, etc. The controller 904 includes any type of control system (e.g., an Arduino™ microcontroller or an Application Specific Integrated Circuit ("ASIC")) that is configured to provide open or closed loop system control using inputs from sensors to control lighting and oil flow.

In this example, the controller 904 is separately electrically connected to lamp assemblies 108a-d via respective electrical connectors 111a and 111b. The electrical connectors 111 are disposed within respective connection lines 602a and 602b. The controller 904 uses the separate connection lines 602 to provide separate control to the lamp assemblies 108 within the respective connection lines 602. For example, the controller 904 may provide power to the lamp assemblies 108a and 108b while placing lamp assemblies 108c and 108d into an off state.

The example controller 904 is communicatively coupled to the pumps 906. The controller 906 may provide digital instructions or an analog PWM voltage to operate the pumps 906. In this example, the system 900 includes a separate pump 906 for each of the connection lines 602 so that the controller 904 can independently control the flow of immersion oil to the respective lamp assemblies 108. In other embodiments, a single pump 906 is used to provide oil to one or more connection lines 602.

The example pumps 906 include any type of component for providing immersion oil to the connection lines 602. For example, the pumps 906 can include displacement pumps, gear pumps, screw pumps, roots-type pumps, peristaltic pumps, plunger pumps, hydraulic pumps, velocity pumps, etc. Responsive to receiving a control signal (e.g., a voltage) from the controller 904, the pumps 906 move immersion oil from the container 908 to the respective connection lines 602. The pumps 906 can be configured to pump oil at varying velocities. Alternatively, the pumps 906 may be configured to operate in a binary state (e.g., On/Off). While the pumps 906 are shown as being located at the entrance of the connection lines 602, in other embodiments the pumps 906 may be located at the exit of the connection lines 602. In these other embodiments, the pumps 906 are configured to pull immersion oil through the connection lines 602.

The example immersion oil container 908 may be any type of tank to store immersion oil. In some examples, the container 908 may include a jacket that is positioned along a portion of the vessel 102. Further, the oil container 908 may include a component that provides active cooling or heating.

In the illustrated example of FIG. 9, the controller 904 is configured to control a voltage, frequency, and PWM (e.g., duty cycle) of power applied to the lamp assemblies 108. For example, the controller 904 is configured to provide a voltage between 8.8 and 12 volts to each of the lamp assemblies 108. In other examples, the controller 904 may be configured to provide a voltage between 0 and 24 volts to the lamp assemblies 108. The applied voltage is used to control the intensity of light transmitted from the lamp assemblies 108. In examples where the LEDs (or other light sources) emit light proportional to the applied voltage, the controller 904 is configured to provide a voltage such that the LEDs emit light at a light intensity optimal for growth of the current culture.

The frequency of light emitted by the LEDs may be in the range between 390 to 700 nm. The frequency of light is based on the type of light source. In some examples, the controller 904 is configured to select which LEDs are activated to achieve the desired light frequency. For instance, each of the lamp assemblies 108 may include red, green, and blue LEDs. The lamp assemblies 108 may also include one or more mirrors to combine the light transmitted from the LEDs. The controller 904 may be configured to time the pulsing of the different colored LEDs to achieve a resulting light frequency that is optimal for the target culture. Alternatively, light filters may be applied to the lamp assemblies 108 to achieve the desired light frequency.

In addition to controlling the magnitude of the voltage, the controller 904 is also configured to cycle the voltage at a specified PWM. For example, the controller 904 may cycle the lamp assemblies 108 over a 100 millisecond (ms) time period such that the LEDs are on for 75% of the time (e.g., 75 ms) and off for 25% of the time. The controller 904 is accordingly programmed (or provided instructions) for a duty cycle and time period. While a 75% duty cycle and 100 ms time period was used as an example, the controller 904 can be programmed to operate the lamp assemblies 108 using any duty cycle and time period.

The controller 904 is also configured to control the flow of immersion oil through the lamp assemblies 108 to regulate the temperature within the vessel 102. The controller 904 uses instructions provided from the workstation 902 to determine how the power and oil flow is to be controlled. It should be appreciated that different types of cultures have optimal growth settings and as a result, the controller 904 can be programmed based on the culture to be grown within the vessel 102.

The example controller 904 is also configured to monitor conditions within the vessel 102 and report these conditions to the workstation 902. In this embodiment, the vessel 102 includes temperature sensors 912, which are communicatively coupled to the controller 904. The controller 904 records temperature data provided by the sensors 912 and periodically transmits the temperatures to the workstation 902. The controller 904 is also configured to report current operating conditions including, for example, voltage, frequency, and PWM applied to each lamp assembly, a duration of operation, and/or detected diagnostic faults within the system 900 (e.g., a broken lamp assembly or obstruction within a connection line 602), communication interference with the workstation 902, etc.

Figure 10:
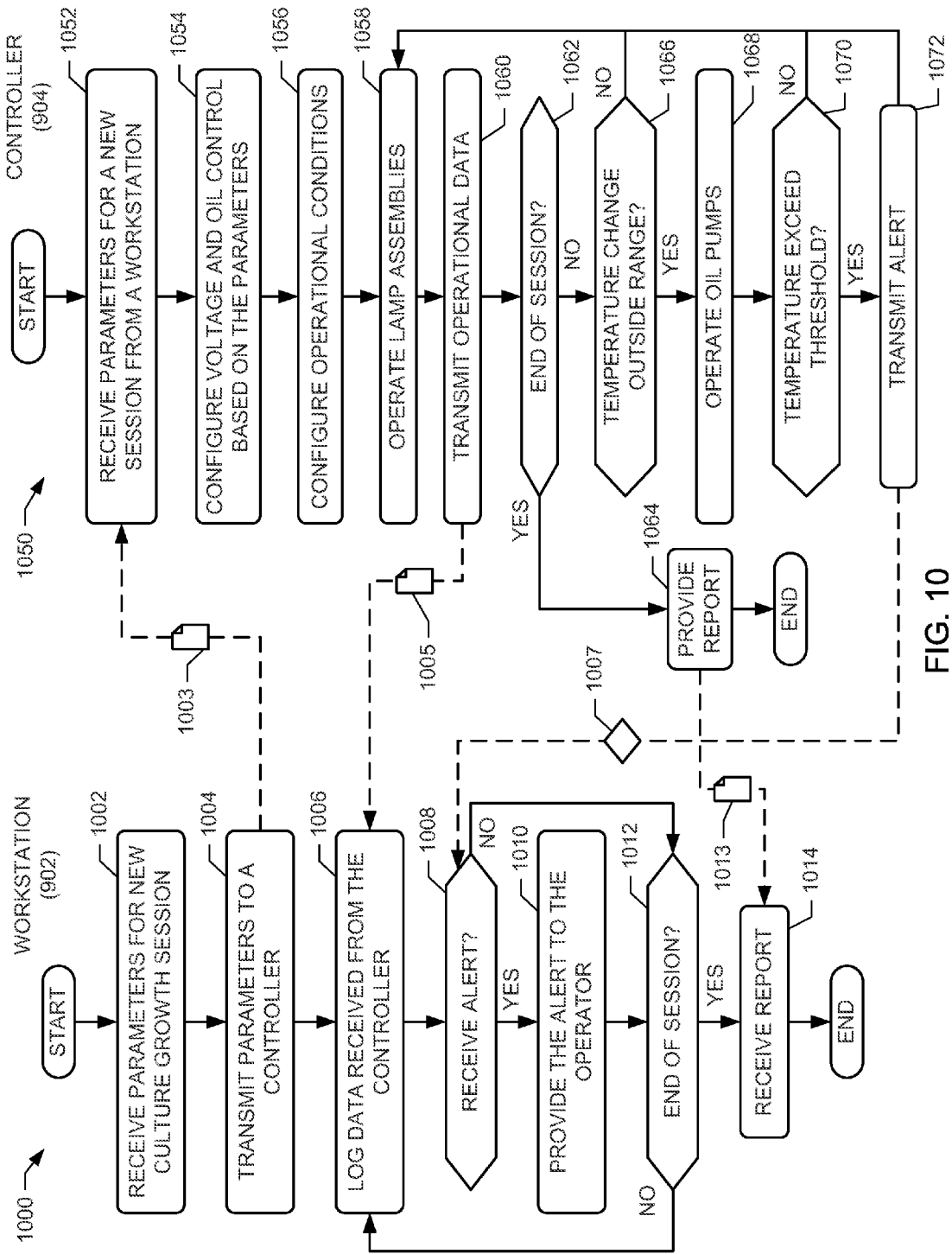
FIG. 10 shows a flow diagram illustrating example procedures to control the growth of a culture, according to an example embodiment of the present invention.

FIG. 10 shows a flow diagram illustrating example procedures 1000 and 1050 to manage the growth of a culture within the vessel 102 of FIG. 9, according to an example embodiment of the present invention. The example procedures 1000 and 1050 may be carried out by, for example, the workstation 902, the controller 904, the pumps 906, and/or the lamp assemblies 108 described in conjunction with FIG. 9. Although the procedures 1000 and 1050 are described with reference to the flow diagram illustrated in FIG. 10, it will be appreciated that many other methods of performing the acts associated with the procedures 1000 and 1050 may be used. For example, the order of many of the blocks may be changed, certain blocks may be combined with other blocks, and many of the blocks described may be optional.

It will be appreciated that all of the disclosed procedures described herein can be implemented using one or more computer programs or components. These components may be provided as a series of computer instructions on any conventional computer-readable medium, including RAM, ROM, flash memory, magnetic or optical disks, optical memory, or other storage media. The instructions may be configured to be executed by a processor (e.g., the workstation 902 and/or the controller 904), which when executing the series of computer instructions performs or facilitates the performance of all or part of the disclosed methods and procedures.

The example procedure 1000 begins when an operator uses the workstation 902 to program a routine for a session to grow a new culture (e.g., a photosynthetic algae culture) (block 1002). The operator specifies a time period of 50 ms and a duty cycle of 55%. The operator also specifies that the voltage applied to the LEDs is to be 10.75 volts to generate a desired light intensity. The operator further specifies that the culture is to be grown over a two day period and that the temperature of the medium 103 is not to exceed 105° C. The operator moreover selects to receive alerts when any issues are detected with any of the lamp assemblies 108 and a report that graphs the temperature of the vessel 102 over time.

After programming the routine, the operator instructs the workstation 902 to transmit instructions 1003 (e.g., parameters) to the controller 904 (block 1004). The instructions 1003 include the programmed routine and may be formatted in a programming language compatible with the controller 904. The workstation 902 then begins to receive and store process data 1005 from the controller 904 (block 1006). The process data 1005 includes operational and diagnostic information indicative of the process at the vessel 102. The workstation 902 may receive a relatively constant stream of process data 1005 as the data is processed and transmitted by the controller 904. Alternatively, the workstation 902 may periodically receive the process data 1005 from the controller 904.

The workstation 902 analyzes the process data 1005 for any alerts (block 1008). Additionally or alternatively, the workstation 902 determines whether an alert message 1007 was received from the controller 904. If an alert was received, the workstation 902 notifies an operator of the alert (block 1010). The notification can include, for example, a text message, an e-mail, an audio message, etc. indicating the contents of the alert. In the illustrated example, an alert can include an indication that a temperature of the vessel 102 is greater than the 105° C. threshold. Alternatively, the alert can include information indicating that one or more of the lamp assemblies are inoperable. Moreover, the alert can include information indicating that either of the pumps 906 is not performing as expected.

In the illustrated example of FIG. 10, the workstation 902 determines whether the session has expired after providing an alert to the operator (block 1012). In other embodiments, the workstation 902 may instruct the controller 904 to pause the process until an operator responds to the alert. In yet other embodiments, the workstation 902 may provide the controller 904 instructions for responding to an alert. For instance, after detecting that the lamp assembly 108b is inoperative, the workstation 902 provides the controller 904 instructions changing the duty cycle, time period, and voltage for the other lamp assemblies 108a, 108c, and 108d to compensate for the loss of light.

Responsive to not receiving an alert, the workstation 902 determines whether the session (e.g., the programmed two day operating time) has ended (block 1012). Responsive to determining the session has ended, the workstation 902 receives a report 1013 that includes the monitored temperature of the vessel 102 over the two day period (block 1014). The example procedure 1000 then ends. Alternatively, the example procedure 1000 returns to block 1002 for the next session. However, if the workstation 902 determines that the session has not ended (block 1012), the workstation 902 returns to receiving process data 1005 from the controller (block 1006). The example procedure 1000 then continues until the session expires.

The example procedure 1050 begins when the controller 904 receives operation instructions 1003 from the workstation 902 (block 1052). The example controller 904 then configures its operation to provide power to lamp assemblies 108 based on the instructions 1003 (block 1054). The configuration can include setting parameters for output drives so that the lamp assemblies 108 receive 10.75 volts at a 55% duty cycle of a 50 ms time period. The example controller 904 also configures its connection to the pumps 906. This configuration can include operating the pumps 906 so that there is sufficient immersion oil within the lamp assemblies 108.

The example controller 904 also configures operation conditions including, for example, an allowable temperature ranges for the vessel 102, alert threshold temperatures for the vessel 102, diagnostic settings, etc. (block 1056). The controller 904 also determines which process data is to be transmitted to the workstation 902 and which data is to be included within a report. The configuration can further include calibration of the temperature sensors 912 and/or the lamp assemblies 108.

After configuration, the controller 904 operates the lamp assemblies at the specified voltage and duty cycle (block 1058). The example controller 904 also begins receiving outputs from the temperature sensors 912. For instance, temperature sensor 912a reports the temperature in the liquid medium culture 103, temperature sensor 912b reports the temperature within the lamp assembly 108a, and temperature sensor 912c reports the temperature of connection line 602b. It should be appreciated that in other examples, only one of the temperature sensors 912 may be used. It should also be appreciated that in other examples, the controller 904 may be configured to receive outputs from other types of sensors (e.g., pH sensors, salinity sensors, light sensors, chemical sensors, etc.

In this example, the controller 904 transmits the temperature data as the process data (e.g., operational data) 1005 (block 1060). The process data 1005 can also include any faults detected within the vessel 102 and/or within the controller 904. The process data 1005 can further include the voltage and duty cycle applied to the lamp assemblies 108 and whether the pumps 906 are being operated.

The example controller 904 then determines whether the session should end (e.g., the two day period) (block 1062). Responsive to determining that the session should end, the example controller 904 compiles collected data, generates a report, and transmits the report 1013 to the workstation 902 (block 1064). In other embodiments, the example controller 904 ends the session and notifies the workstation 902 that the session has ended without providing a report. In these other embodiments, the controller 904 may not have the capability of generating a report. Instead, the controller 904 may provide a log or data structure of collected data at the end of the session. At the end of the session, the example procedure 1050 ends. Alternatively, the example procedure 1050 returns to block 1052 to begin a session for another culture.

Returning to block 1062, if the session has not ended, the controller 904 compares the temperature outputs from the sensors 912 to pre-specified temperatures (block 1066). The controller 904 performs this comparison to determine whether action should be taken to actively change the temperature within the vessel 102. For example, if the temperature is outside of a specified allowable range, the controller 904 operates the pumps 906 to circulate cooler (or warmer) oil through the vessel 102 (block 1068). The controller 904 continues to operate the pumps 906 until the temperature is within the allowable range. Additionally or alternatively, the controller 904 may also change the intensity of the lamp assemblies 108 and/or the duty cycle to modify the temperature. For instance, lowering the voltage applied to the lamp assemblies 108 reduces the amount of heat transmitted to the vessel 102. Moreover, changing the duty cycle to have more time in an 'Off' state also reduces the amount of heat transmitted to the vessel 102.

The example controller 904 also determines whether the temperature of the vessel 102 exceeds a threshold (block 1070). Responsive to determining the temperature exceeds a threshold, the controller 904 transmits an alert message 1007 to the workstation 902 (block 1072). The controller 904 continues to operate the lamp assemblies 108 until further instruction is provided by the workstation 102 or until the session ends.

A photosynthetic microorganism such as an alga may be cultivated and/or propagated with the photobioreactor as disclosed herein. Generally, prior to filling the interior volume of the vessel of the photobioreactor with a culture medium, the interior of the photobioreactor is sanitized by exposing it to a sterilizing gas, a hypochlorite solution or the like. Following sanitization, water is introduced into the vessel via a pressurized water line. The vessel is filled with water to a predetermined depth. In some embodiments, the vessel is filed such that the surface of the culture medium will be below an exit port. Nutrients and inocula (e.g., one or more photosynthetic organisms such as an alga) are introduced into the vessel by removing the lid or introducing them through an access port in the vessel or lid. The pH and temperature of the medium may be monitored throughout the photobioreaction by a temperature probe and a pH probe. The photobioreaction is initiated by supplying electrical power to the lamp assembly and optionally initiating sparging of an appropriate gas mixture via an inlet tube. The progress of the photobioreaction may be monitored with a calibrated density detector. Adjustments to the pH or the composition of the culture medium may be effected by introducing materials through the lid or an access port in the vessel or lid.

In some embodiments, a starter culture of each photosynthetic microorganism to be added to the vessel may be grown. After the starter culture reaches an optimal density, a portion of the culture may be added to the vessel. In some embodiments, where two or more types (e.g., species or strains) of microorganisms are added to the vessel, an equal number of each type of photosynthetic microorganism may be added to the vessel. Alternatively, an unequal number of each strain of photosynthetic microorganism may be added to the vessel.

When the photosynthetic microorganisms are ready to harvest, the light source and optional sparging gas are turned off and the medium containing the photosynthetic microorganisms is collected. In an embodiment, the medium and photosynthetic microorganism may be collected via the opening of an optional valve located on vessel wall. In a further embodiment, a pump may be used to expel the medium and photosynthetic microorganism from the vessel. Alternatively, in embodiments where the vessel comprises a gas inlet (e.g., for $CO_2$ injection), the gas inlet may be reversed to allow static pressure to build up and force the media out via an alternate line. Alternatively, the photosynthetic microorganism may agglomerate and be expelled from the vessel (e.g., by excess air flow) onto a surface external to and apart from the vessel. In other embodiments, an ultrasonic transducer may be used to vaporize the media in the vessel and thereby cause a mass of photosynthetic microorganisms to collect around the transducer where they may subsequently be harvested. Optionally, the vaporized media may be collected and recirculated for use in the photobioreactor. The microorganisms may then be harvested and/or dehydrated by any methods known in the art.

The photobioreactor may further comprise a separating apparatus for separating the removed portion of media containing the photosynthetic microorganisms into a liquid phase and into a solid phase (which contains the microorganisms). The separating apparatus is preferably a filter but depending on the type of microorganisms, other separating means known to one skilled in the art may be used.

In an exemplary method, the photobioreactor disclosed herein may be used to propagate one or more photosynthetic microorganisms (e.g., a polyculture) such as algae that produce biomolecules such as fatty acids, phycobiliproteins such as C-Phycocyanin, allophycocyanin, phycoerythrin, biofuels such as phytol, and other various petrol fuel substitutes. In one embodiment, two or more algae may be propagated together that have natural environments that are similar in salinity and dissimilar in temperature such as algae selected from the group consisting of *isochrysis aff. galbana, pavlova lutheri, arthrospira platensis, chlorella pyrenoidosa, synechococcus elongates*, including naturally occurring or genetically modified/recombinant strains of the foregoing.

Such a combination of algae provides the benefit that while the temperature of the liquid media in the vessel may change, there will typically be at least one alga that propagates at a low temperature and at least one alga that propagates at a higher temperature. Algae are then propagated in the photobioreactor as provided herein and ultimately separated from the growth medium after the algae reach a desired density. After separation of the algae from the growth media, DHA is obtained from the algae and optionally purified.

Without further description, it is believed that one of ordinary skill in the art may, using the preceding description and the following illustrative examples, make and utilize the agents of the present disclosure and practice the claimed methods. The following working examples are provided to facilitate the practice of the present disclosure, and are not to be construed as limiting in any way the remainder of the disclosure.

EXAMPLES

Example 1

Construction of Pebble

A pebble (also referred to herein as lamp assembly), for practice of the methods provided herein, may be constructed by any known methods and materials in the art and comprises a light source and a barrier surrounding the light source.

A. Pebble Assembly

A pebble may be constructed from a circuit panel (e.g., pentagonal shaped panels) with pre-mounted LED array. A pebble section (e.g., two or more affixed pentagon-shaped circuit boards) is prepared by bonding each with liquid cyanoacrylate (1 three-panel section, 2 four-panel sections) along internal edges, not connecting one section to the other. The cyanoacrylate is given approximately 3 hours to dry. After drying, three sections are press fit together into a dodecahedral shape, with one side of the dodecahedron kept open for connectivity purposes (e.g., wire access), and allowed to dry and settle into shape overnight. Next, the three main sections are taken apart. On each of the two 4-sided pebble sections, using lead-free solder only, ground connections with 28 gauge wire are soldered to the central panel. This is repeated with a 12-volt connection, making connection to same central panel as ground and with 3-sided portion, using any of the 3 sides as the main connection panel. The ground connection from the main panel on the 3-panel section is then connected to the main panel on one of the 4-panel sections with 28 gauge wire and lead-free solder. The second 4-panel section's main panel is connected to the first 4-panel section on the panel on the far end on the section adjacent to the main panel (sharing a side with the main panel, with only one other side bonded to a panel). To this last panel, now connecting all the ground on one circuit and all the 12V connection on another, solder a 22-gauge wire to each circuit (length to be determined by even pebble distribution throughout barrel (approximately 10"-40")). Next, the panels are press fit together, taking care to carefully arrange wires within. The pebbles are then filled with 10-12 glass beads for weight.

B. Pebble Case Assembly

A case for the pebble may be prepared using a polyethylene (Nalgene) jar with dimensions to allow for the circumference of the pebble. A ¼" hole is drilled in the center of the lid of the jar. Next, a silicone gasket is inserted ¼" through the wall of the lid. A male ¼" brass through-wall barbed fitting is then screwed from underside of lid and attached to a ¼" silicone gasket from top of the lid. A female ¼" brass fitting is then screwed to the male fitting from the top of the lid. Next, 1½" of ¼" inner diameter flexible silicone tubing is attached to the lid gasket using cyanoacrylate as a bonding agent. ¼" OD rigid LLDPE white tubing (length to be determined by optimal pebble dispersion within barrel) is then attached to connection tubing using cyanoacrylate as a bonding agent. The base of a jar is then filled with a number of clear glass beads (e.g., 14) for weight and light dispersion. The assembled pebble is then placed within the jar and seated upon glass beads. 22 gauge wire is then threaded through the gasket and tubing. Subsequently, the jar is filled to maximum with white mineral oil and the lid is tightly screwed on expelling as much air as possible. Excess oil adhered to the outside of the jar is removed and the jar is then rinsed with reverse osmosis water.

C. Pebble Case Embodiments

FIGS. 12 to 35 are diagrams showing embodiments of lamp assemblies. In each of the embodiments, the lamp assemblies 108 include circuit boards 113 connected together in a specific geometry based on the dimensions of the casing. Each of the lamp assemblies includes an inlet and an outlet to facilitate the flow of immersion oil. The inlet and outlet are dimensioned to mechanically connect to the connection lines 602. Further, the inlet includes electrical connectors 111 (which are not shown).

For example, FIGS. 12 and 13 show a lamp assembly 108 that includes six circuit boards 113 connected together to form a double-pyramid. The lamp assembly 108 includes a casing 1202 that is dimensioned to accommodate the six circuit boards. In particular, the casing 1202 is bulb-shaped, which provides an efficient propagation of light to a surrounding liquid culture medium. The lamp assembly 108 receives immersion oil via the inlet 1204. The immersion oil exits the lamp assembly 108 at output 1206. Further, electrical connectors 111 are routed through the inlet to the circuit boards 113 (not shown). In some examples, the electrical connectors 111 contact a first circuit board. Electrical traces are used to electrically connect the other circuit boards to the first circuit board. In other examples, each of the circuit boards 113 is connected to the electrical connectors 111.

Figure 14:
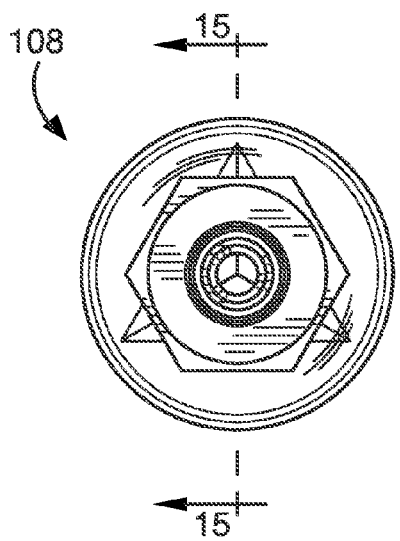
Figure 15:
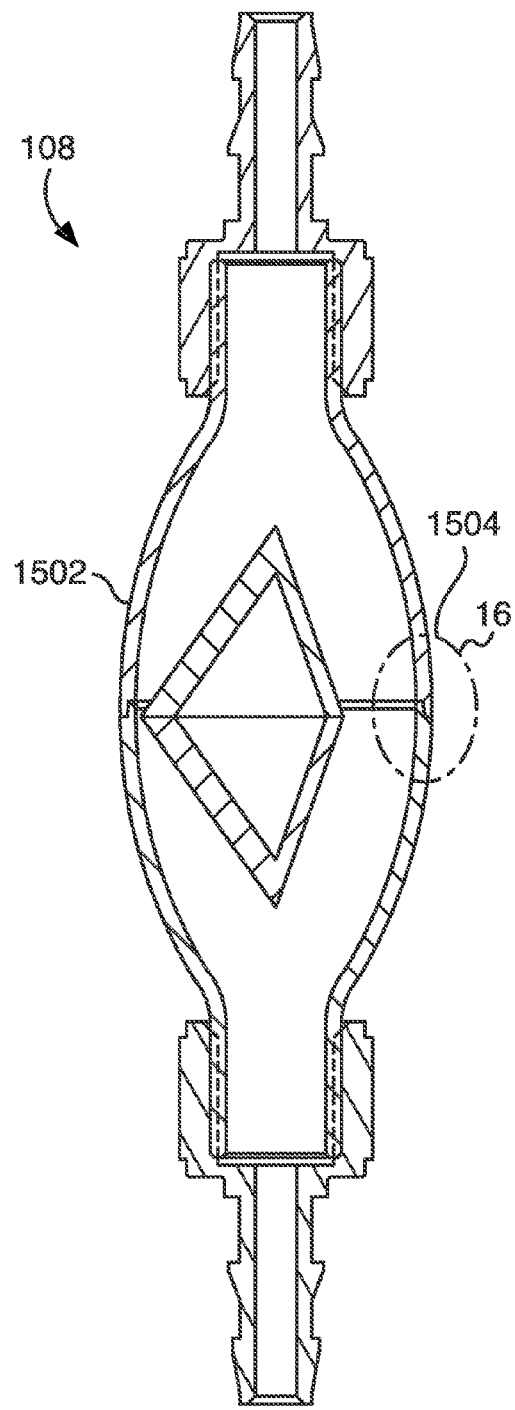
Figure 16:
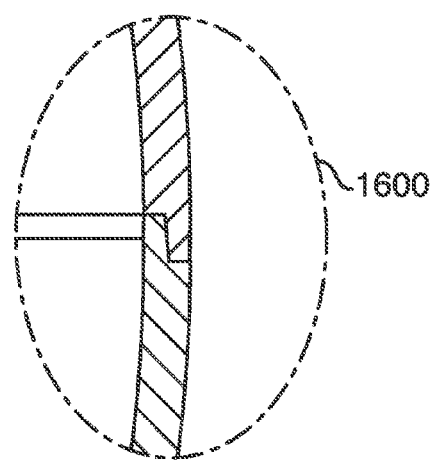
Figure 17:
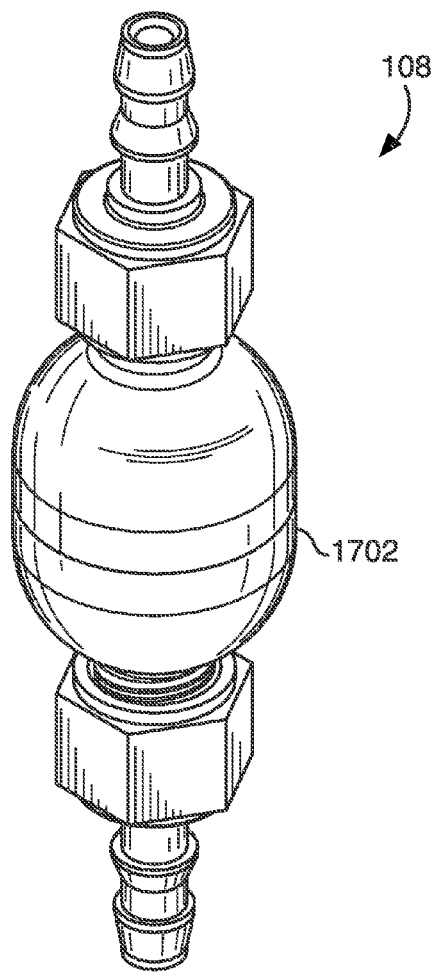
Figure 18:
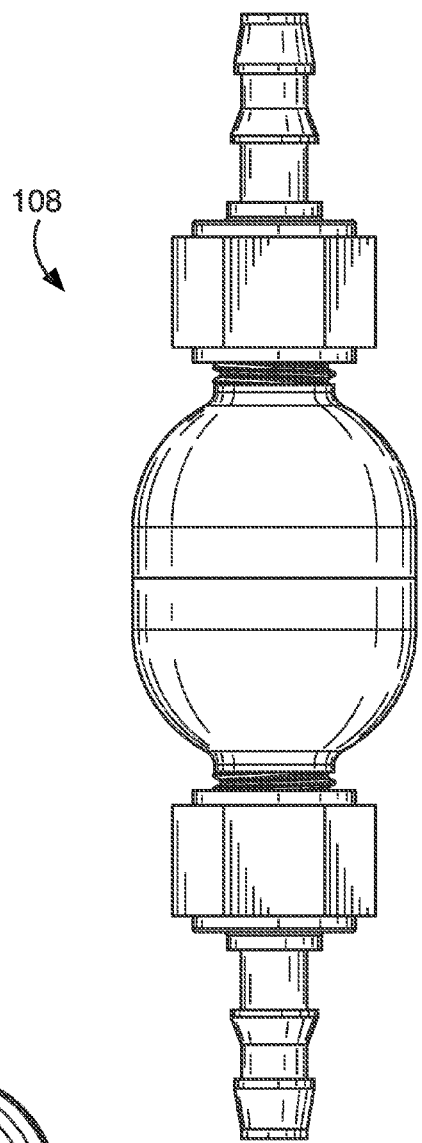
Figure 19:
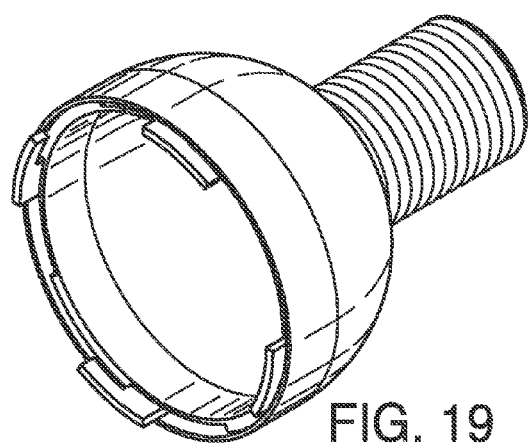
Figure 20:
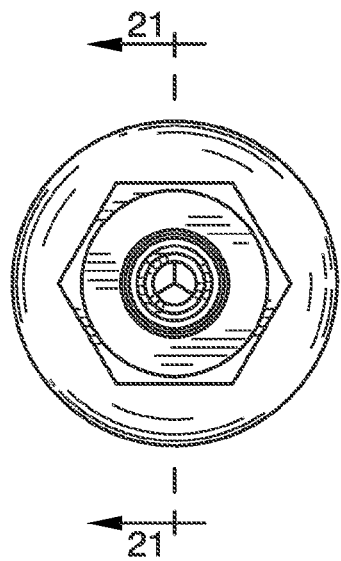

FIGS. 14 to 16 show schematic diagrams of the lamp assembly 108 of FIGS. 12 and 13. In particular, FIG. 14 shows a top-perspective view of the lamp assembly and FIG. 16 shows an enlarged view of a case connection 1504 of the casing 1502 shown in FIG. 15. In this embodiment, the casing 1502 is formed as two separate halves joined together at joint 1600. The casing 1502 is formed as separate halves to enable the circuit boards to be installed inside the casing 1502. As shown in FIGS. 15 and 16, the joint 1600 may be mechanically sealed by the dimensioning of each half of the casing 1502. Alternatively, the joint 1600 may be chemically sealed using an (substantially transparent) adhesive.

Figure 21:
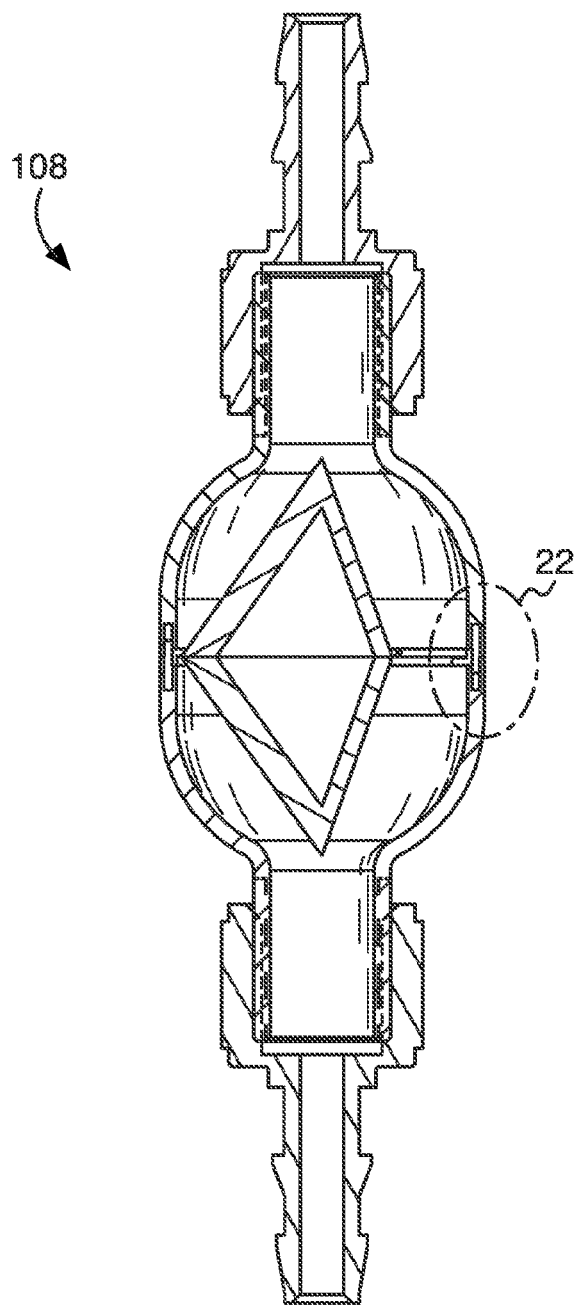
Figure 22:
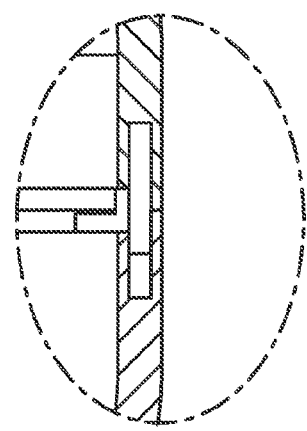

FIGS. 17 to 22 show another embodiment of a lamp assembly 108. In this embodiment, a casing 1702 is more spherical than the casing 1502. In addition, FIGS. 19 to 22 shows that the casing 1702 is formed of two halves that are connected together using tabs 1902. In particular, FIGS. 21 and 22 show how the halves of the casing 1702 are mechanically connected by each of the tabs contacting a corresponding reception area.

Figure 23:
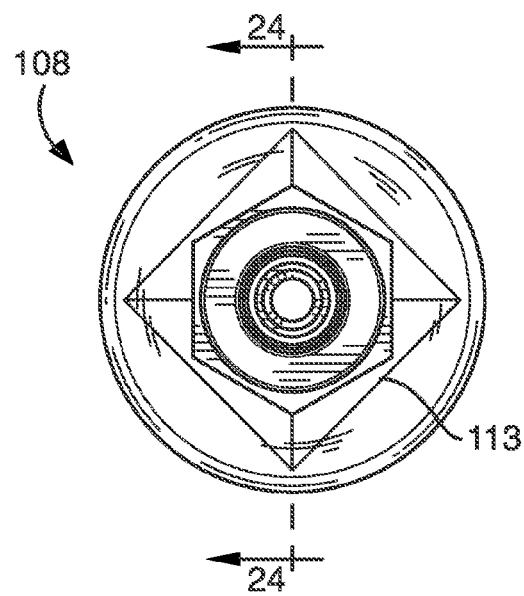
Figure 24:
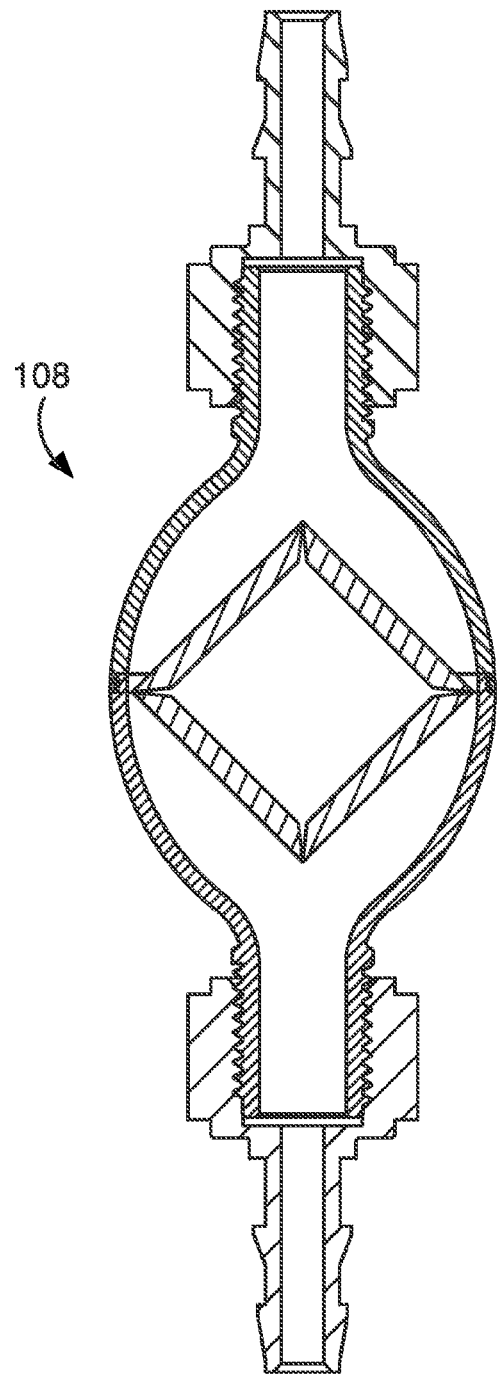

FIGS. 23 to 28 show different embodiments of circuit boards within the lamp assemblies. In particular, FIG. 23 shows a top-perspective view of a lamp assembly 108 shown in FIG. 24. The lamp assembly 108 includes a triangular matrix of circuit boards 113 connected together to form a cube. The connection of the circuit boards 113 enables light to be transmitted in substantially all directions for optimal culture growth.

Figure 27:
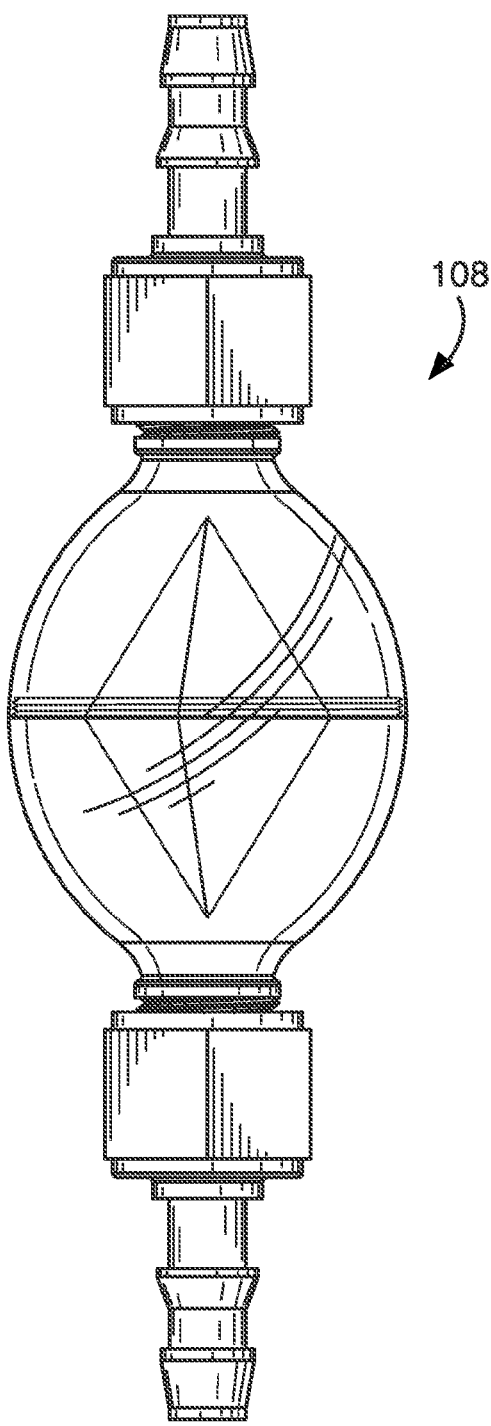
Figure 28:
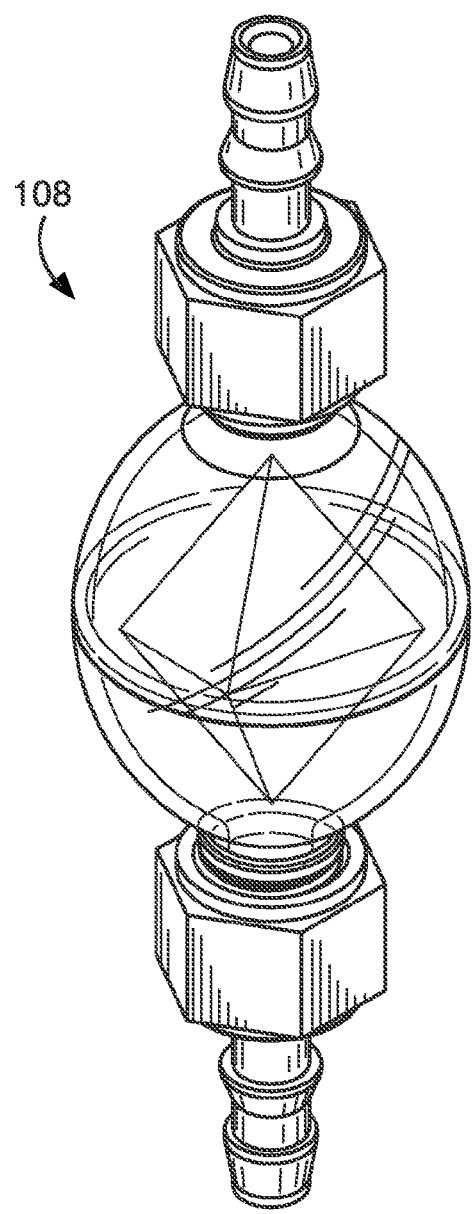

FIG. 25 shows a diagram of an eight-sided cube formed from triangular circuit boards 113. FIG. 26 shows a diagram of three-sided cube formed from triangular circuit boards 113. FIG. 27 shows a diagram of six-sided double pyramid formed from triangular circuit boards 113. FIG. 28 shows a diagram of six-sided cube formed from triangular circuit boards 113. It should be appreciated that other embodiments can include greater number of sides to form a structure that is substantially spherical.

Example 2

Construction of Photobioreactor

A photobioreactor for practice of the methods provided herein may be constructed by any known methods and materials in the art and is constructed by assembly of a barrel, lid, and $CO_2$ stone (also referred to herein as a lamp assembly).

A. Assembly of Barrel

In an exemplary method, using a standard 60 gallon polypropylene barrel (open head), the barrel is prepared by drilling 8 equidistant ½" holes 4½" from the base of the barrel. Equidistant between two adjacent holes, a 9th ½" hole is drilled 2½" from the base of the barrel. Next, using an exacto blade, excess plastic is removed and the drill hole edges are smoothed.

From the inside of the barrel, using a wrench, a ¼" barbed male nylon fitting is screwed through each of the drilled holes. Next, from outside the barrel, ½" silicone washer fittings are then attached onto the barbed male fittings which are then screwed onto ¼" nylon barbed female fittings and tightened. 1¾" length of rigid (thick wall) ¼" tygon tubing is then attached to the male fitting on the outside of the barrel. Subsequently, ½" length of black ⅛" black silicone tubing is slid over the barbed fitting of a large air stone. The air stone assembly is then inserted into the tygon tubing and the process is repeated for all ½" fittings at the 4½" height. A 3" length of rigid tygon tubing (thick wall) is then attached to an external, female barbed fitting. This process is then repeated for all 9 fittings. Next, 130" of rigid white LLPDE tubing is attached to all 8 fittings at the 4½" height. A push-to-connect adaptor fitting[i] and push-to-connect ball valve are then attached to the 9th (2½" height) fitting. Subsequently, 2" of clear ¼" tygon tubing (thin wall) is attached to each of the 130" white rigid LLDPE tubes. 8½" lengths of ⅛" black silicone tubing are then connected to barbed fittings of an 8-way polypropylene manifold. Each rigid LLPDE 130" tube is connected to the 2" long clear tygon tubing connector (thin wall), which is then connect to the manifold.

B. Assembly of Lid

Figure 11A:
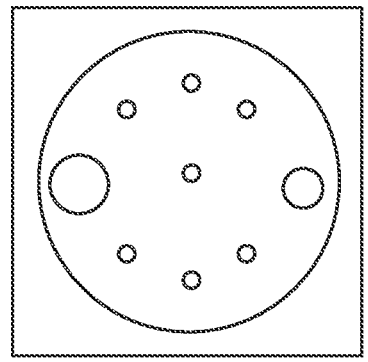
FIG. 11 shows an illustrative vessel lid (A) and illustrative pebble configurations (B).

In an exemplary method, seven holes are drilled into a black polypropylene lid using a ½" plastic drill bit, with a configuration as shown in FIG. 11A.

Figure 11B:
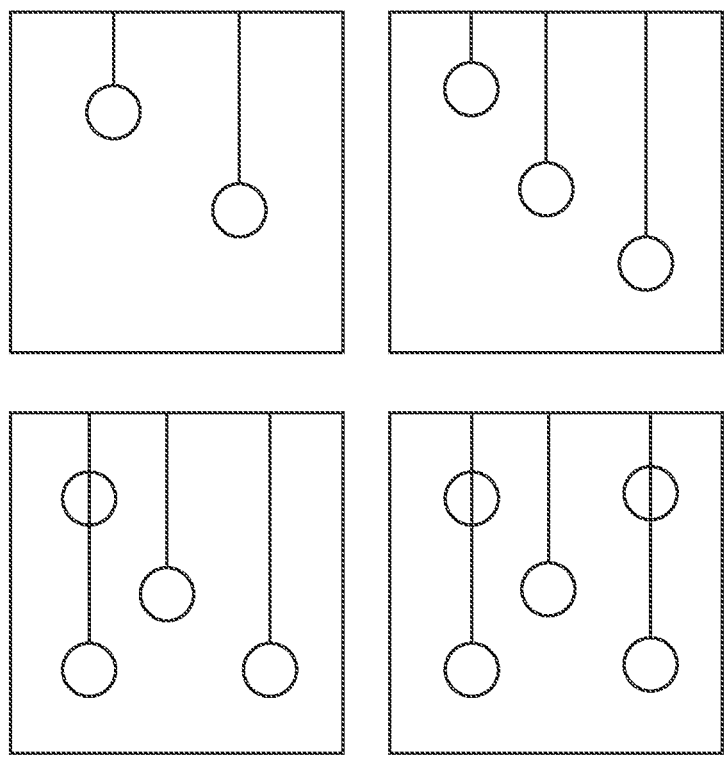

Any excess plastic is then cleaned away from the drilled edges with an exacto blade and smoothed. From the bottom of the lid, ¼" male barbed nylon fittings are placed in the holes and screwed together with ¼" female barbed nylon fittings from the top side of the lid. Silicone washers may be placed between the female fitting and the top side of the lid. Distribution of lights using other fittings to be determined by the strain(s) intended for cultivation. Next, 2" length of rigid tygon tubing (thick wall) is attached to each male nylon ¼" fitting in the lid. A length of rigid LLPDE tubing is then attached to each connection, except the central location (length to be determined by even distribution of pebbles throughout barrels) as shown in FIG. 11B.

Subsequently, 2" rigid tygon connector tubing is then connected to an end of the rigid LLPDE tubing. The pebble wiring is run through the rigid LLPDE tubing and out through the barbed fittings in the top of the lid. Connector tubing is then attached to the base of pebble's brass fitting using liquid cyanoacrylate as a binding agent. This process is repeated as needed for desired pebble distribution. For protection from salt contamination, flexible latex tubing is attached to top, female end of lid fittings and around all wires as needed based on distribution of saltwater spray.

C. Assembly of $CO_2$ Stone

In an exemplary method, 30" length of rigid white LLDPE tubing is attached to a central fitting with connector tube. Next, the dome apex is marked on the female hemisphere of a 2 part 100 mm clear acrylic sphere. The corners of an equidistant triangle, with sides approximately 2" in length, are then marked out on the male hemisphere and centered on the dome apex. A ¼" rotary tool grinding bit is then used to make preliminary guide holes for each marking. Next, a ½" rubberized grinding bit is used to make final holes centered on guide holes. Excess plastic from drilling is removed from the holes is removed with clippers and an exacto blade until the holes are smooth. A ½" rubber through-wall gasket is then attached to each of the holes. Next, a ½" brass through-wall barbed fitting is attached to the central hole in the female hemisphere with a gasket. The male hemisphere is then filled with 450 grams of clear glass beads. Subsequently, cyanoacrylic bonding agent is applied to the bottom male hemisphere and the male and female hemisphere are press fit together. The cyanoacrylic bonding agent is allowed to dry for approximately one hour. Next, 2" length of rigid tygon is attached to a brass fitting barb using cyanoacrylic bonding agent. Again, the cyanoacrylic bonding agent is allowed to dry for approximately one hour. The assembled sphere and connector tube are then attached to rigid white tubing attached to central lid fitting.

Example 3

Use of Photobioreactor for Growth of Photosynthetic Microorganism

A photobioreactor provided herein may be used in methods for growing one or more photosynthetic microorganisms. Such methods may employ a four step process including: 1.) determining optimal environmental conditions (OEC); 2.) staging and inoculation of production environment; 3.) growing a photosynthetic microorganism to an extractable mass; and 4.) selective extracting of mature cells.

A. Determination of Optimal Environmental Conditions (OEC)

When starting up a new or unknown strain it is necessary to determine optimal values for all growth variables including: salinity, nutrient concentrations, EM frequency (RWB ratio), EM cycle, and rate of airflow. OEC may be determined by using an approximation of natural environmental conditions (NEC) as a starting point. Beginning with three Generation 4 reactor chambers (2 liter capacity) for each variable to be tested, process of elimination is used to narrow down the options. For example, chamber 1 comprises an experimental variable at a concentration 60% greater than its NEC, chamber 2 comprises the experimental variable at its NEC, and chamber 3 comprises the experimental variable at a concentration 60% less than its NEC. Speed of growth of the strain is determined by observation of the rate in change of Diffused Optical Density (DOD). If/then for DOD:

If C1>C2>C3, Then Round 2 baseline=C1 with variances of +/−15%;

If C2>C1&C3, Then Round 2 baseline=C2 with variances of +/−15%;

If C3>C2>C1, Then Round 2 baseline=C3 with variances of +/−15%

This process is continued for 4 rounds and repeated for each experimental variable to determine the new strain's OEC values.

B. Staging and Inoculation of Production Environment

Using the OEC values determined above, a Generation 5 Reactor (30 liter capacity) is prepared to those levels determined in A above. Salinity levels are set, pumps are activated, and nutrients are added to the reactor in accordance with such predetermined levels. The nutrients are given approximately two hours to mix without light. After the nutrients have mixed, the Reactor is seeded with at least 10% live culture. Based on continuous testing of water nutrient levels, the culture is fed as needed for the next 3-10 days based on the growth rate of the strain. When DOD has reached a level where individual LED's are no longer visible, a generation 7 reactor is prepared using the same method as described above with 90% of the culture in Generation 5 Reactor as inoculation for Generation 7 Reactor.

C. Growth to Extractable Mass

Once growth is established in the Generation 7 Reactor, the following conditions should be continually monitored: pH, ammonia, nitrate, nitrite, phosphate, dissolved $CO_2$, dissolved $O_2$, system air flow, system pressure, and diffused optical density. As these conditions deviate from OEC in response to microorganism growth steps must be taken to maintain OEC across these parameters. For example, if a Gen 7 cyanobacterial culture has tripled in density over a 48 hour period (observable through increase in DOD and Turbidity) and Ammonia has decreased to 0 ppm then a diluted addition of concentrated fertilizer should be added to return Ammonia to OEC. Additionally, for example, if a Gen 7 culture has been run continuously for 3 months and in response to multiple feedings and a buildup of digestive waste pH has increased off OEC to 8.4 then a diluted addition of organic acid (i.e. citric acid) should be added to return pH to that culture's OEC for pH.

As exponential growth of photosynthetic microorganisms continues, DOD will continue to increase in proportion with culture density. When culture density has doubled three times from the point of its 10% inoculation it is at an ideal point to provide seed inoculation to other reactors. At a 10% level of inoculation, the culture can be used to seed 9 other reactors of comparable size with enough mass left over to self-inoculate its own restart. At a given point culture density will reach a level where the reactor primary fluid can no longer hold the culture in suspension. This point is identified by the increased levels of accumulation/agglomeration in low flow points along the reactor bottom and sides in the presence of OEC. The point at which the system tips toward this condition will be referred to as Peak Suspended Mass (PSM). When PSM is achieved the culture must be put through selective extraction, comprehensive extraction or used to seed other reactors if growth rates are to be maintained. Time to PSM and culture density at PSM vary widely depending on strain and OEM.

D. Selective Extraction of Mature Cells

Prior to the point when PSM is achieved, one of two extraction configurations must be established: 1.) Gen 7 Outlet Valve=>Pump=>Filter=>Gen 7 Return; or 2.) Gen 7 Outlet Valve=>Filter=>Pump=>Gen 7 Return. The configuration is determined based on the characteristics of the strain being filtered. The effectiveness of selective filtration is based on the size variance between mature and immature cells in the given strain(s) and proper selection of the pore diameter of the filtration medium. Filtration pore diameter should be greater than the diameter of the immature cells and less than the diameter of the mature cells by a preferred margin of >25%. Once one of the above configurations is set and PSM is achieved the following steps can be taken: a.) Gen 7 outlet valve moved from CLOSED to OPEN; b.) once pump is primed, pump moved from OFF to ON; c.) once filter bag is full and air pressure has equalized across filter bag, filter cap can be moved from CLOSED to OPEN; d.) optional: if the filter has an installed outlet valve on its return line that valve should be moved from CLOSED to OPEN before the pump and filter are moved to their engaged configuration. At no point should filter pressure exceed 15 psi, 10 psi for smaller diameter bags (<5 microns). Filtration should be monitored closely with new strains as filtration time varies widely with strain.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present disclosure. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the disclosure are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the disclosure (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the disclosure and does not pose a limitation on the scope of the disclosure otherwise claimed. No language in the specification should be construed as indicating any non-claimed element essential to the practice of the disclosure.

Groupings of alternative elements or embodiments of the disclosure disclosed herein are not to be construed as limitations. Each group member can be referred to and claimed individually or in any combination with other members of the group or other elements found herein. It is anticipated that one or more members of a group can be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this disclosure are described herein, including the best mode known to the inventors for carrying out the disclosure. Of course, variations on these described embodiments will become apparent to those of ordinary skill in the art upon reading the foregoing description. The inventor expects skilled artisans to employ such variations as appropriate, and the inventors intend for the disclosure to be practiced otherwise than specifically described herein. Accordingly, this disclosure includes all modifications and equivalents of the subject matter recited in the claims appended hereto as permitted by applicable law. Moreover, any combination of the above-described elements in all possible variations thereof is encompassed by the disclosure unless otherwise indicated herein or otherwise clearly contradicted by context.

Specific embodiments disclosed herein can be further limited in the claims using, consisting of, or and consisting essentially, of language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the disclosure so claimed are inherently or expressly described and enabled herein.

It is to be understood that the embodiments of the disclosure disclosed herein are illustrative of the principles of the present disclosure. Other modifications that can be employed are within the scope of the disclosure. Thus, by way of example, but not of limitation, alternative configurations of the present disclosure can be utilized in accordance with the teachings herein. Accordingly, the present disclosure is not limited to that precisely as shown and described.

While the present disclosure has been described and illustrated herein by references to various specific materials, procedures and examples, it is understood that the disclosure is not restricted to the particular combinations of materials and procedures selected for that purpose. Numerous variations of such details can be implied as will be appreciated by those skilled in the art. It is intended that the specification and examples be considered as exemplary, only, with the true scope and spirit of the disclosure being indicated by the following claims. All references, patents, and patent applications referred to in this application are herein incorporated by reference in their entirety.

The invention claimed is:

1. A photobioreactor for cultivation and/or propagation of a photosynthetic organism comprising:
  a.) a vessel having a wall defining an interior vessel volume; and
  b.) a lamp assembly positioned within the interior vessel volume, wherein the lamp assembly comprises:
    a plurality of circuit boards, each comprising at least three edges, arranged in a substantially spherical shape defining an interior lamp assembly volume, wherein the plurality of circuit boards comprise a first surface in contact with the interior lamp assembly volume and an opposing second surface comprising light emitting diodes (LEDs);
    a barrier that surrounds the plurality of circuit boards forming the substantially spherical shape, said barrier having an inlet and an outlet; and
  c.) a pump for circulating heat dispersal fluid into and out of a void between the barrier and the plurality of circuit boards by way of the inlet and outlet.

2. The bioreactor of claim 1, wherein the vessel is cylindrical and comprises a cylindrical wall, an upper wall, and a lower wall each defining the interior tank volume.

3. The bioreactor of claim 1, wherein the vessel is substantially spherical.

4. The bioreactor of claim 1, wherein the vessel comprises a hole for a gas inlet.

5. The bioreactor of claim 1, wherein the vessel comprises a hole for a gas outlet.

6. The bioreactor of claim 1, wherein the vessel comprises a hole for wiring the lamp assembly.

7. The bioreactor of claim 1, wherein the lamp assembly is positioned in the center of the vessel.

8. The bioreactor of claim 1, wherein two or more lamp assemblies are positioned in the vessel.

9. The bioreactor of claim 8, wherein the two or more lamp assemblies are positioned at different heights in the vessel.

10. The bioreactor of claim 1, wherein three or more lamp assemblies are positioned in the vessel.

11. The bioreactor of claim 10, wherein the three or more lamp assemblies are positioned at different heights in the vessel.

12. The bioreactor of claim 11, wherein the three or more lamp assemblies are positioned in a helical arrangement in the vessel.

13. The photobioreactor of claim 1 wherein the first and second surfaces are independently planar, curved, rigid or flexible.

14. The photobioreactor of claim 1 further comprising a controller configured to control flow of the heat dispersion fluid.

15. The photobioreactor of claim 1 wherein the inlet is operatively connected to a second outlet on a second photobioreactor having substantially the same configuration as said photobioreactor, said second outlet adapted for moving heat dispersal fluid out of a void between a plurality of circuit boards and a barrier on the second photobioreactor.

16. The photobioreactor of claim 15 wherein the outlet is operatively connected to a second inlet on a third photobioreactor having substantially the same configuration as the second photobioreactor, said second inlet adapted for moving heat dispersal fluid into a void between a plurality of circuit boards and a barrier on the third photobioreactor.

17. The photobioreactor of claim 1 wherein the lamp assembly further comprises an electrical connector for connecting the lamp assembly to a power supply that is external to said vessel, wherein the electrical connector is waterproofed so as to prevent contact between the electrical connector and water present in the vessel.

18. A water-submersible lamp assembly for use in cultivation and/or propagation of a photosynthetic organism, the lamp assembly comprising:
  a plurality of circuit boards, each comprising at least three edges, arranged in a substantially spherical shape defining an interior lamp assembly volume, wherein the plurality of circuit boards comprise a first surface in contact with the interior lamp assembly volume and an opposing second surface comprising light emitting diodes (LEDs); and
  a barrier that surrounds the plurality of circuit boards forming the substantially spherical shape, said barrier having an inlet and an outlet adapted for circulating heat dispersal fluid into and out of a void between the plurality of circuit boards and the barrier.

19. The lamp assembly of claim 18, wherein the substantially spherical shaped arrangement of the planar circuit boards has a side devoid of at least one circuit board to permit electrical connectivity.

20. The lamp assembly of claim 18, wherein the circuit boards comprise two or more tabs around their perimeter that form one or more notches that permit the circuit boards to interlock.

21. The lamp assembly of claim 18, wherein the circuit boards are pentagon shaped.

22. The lamp assembly of claim 21, wherein eleven pentagons are joined to form a dodecahedron devoid of one side.

23. The lamp assembly of claim 18, wherein the circuit boards are triangular shaped.

24. The lamp assembly of claim 23, wherein twenty triangles are joined to form an icosahedron devoid of one side.

25. The lamp assembly of claim 18, wherein the LEDs have an emission spectrum suitable for the growth of a photosynthetic organism.

26. The lamp assembly of claim 18, wherein the barrier is plastic.

27. The lamp assembly of claim 26, wherein the plastic permits transmission of light.

28. The lamp assembly of claim 26, wherein the barrier has an open end to permit electrical connectivity.

29. The lamp assembly of claim 26, wherein the void between the plurality of circuit boards and the barrier comprises heat dispersal fluid.

30. The lamp assembly of claim 29, wherein the heat dispersal fluid is mineral oil.

31. The lamp assembly of claim 18, wherein the barrier is substantially spherical.

32. The water-submersible lamp assembly of claim 18 wherein the lamp assembly further comprises a waterproofed electrical connector for connecting the lamp assembly to a power supply.

* * * * *